US012559513B2

(12) United States Patent
Shindo et al.

(10) Patent No.: US 12,559,513 B2
(45) Date of Patent: Feb. 24, 2026

(54) AROMATIC GLYCOSIDE AND METHOD FOR PRODUCING THE GLYCOSIDE

(71) Applicant: CAROTENOID-PRODUCTION TECHNOLOGY CORPORATION (CaroProTech), Ishikawa (JP)

(72) Inventors: Kazutoshi Shindo, Gunma (JP); Norihiko Misawa, Ishikawa (JP)

(73) Assignee: CAROTENOID-PRODUCTION TECHNOLOGY CORPORATION (CAROPROTECH), Ishikawa (JP)

( * ) Notice: Subject to any disclaimer, the term of this patent is extended or adjusted under 35 U.S.C. 154(b) by 406 days.

(21) Appl. No.: 18/130,931

(22) Filed: Apr. 5, 2023

(65) Prior Publication Data

US 2023/0322839 A1 Oct. 12, 2023

(30) Foreign Application Priority Data

Apr. 7, 2022 (JP) .................................. 2022-63690
Jun. 7, 2022 (JP) .................................. 2022-92106
Mar. 24, 2023 (JP) .................................. 2023-47504

(51) Int. Cl.

| | |
|---|---|
| ***C07H 17/07*** | (2006.01) |
| ***A23L 33/00*** | (2016.01) |
| ***A23L 33/105*** | (2016.01) |
| ***A23L 33/125*** | (2016.01) |
| ***C07H 1/08*** | (2006.01) |

(52) U.S. Cl.

CPC ............ *C07H 17/07* (2013.01); *A23L 33/105* (2016.08); *A23L 33/125* (2016.08); *A23L 33/40* (2016.08); *C07H 1/08* (2013.01)

(58) Field of Classification Search

None

See application file for complete search history.

(56) References Cited

FOREIGN PATENT DOCUMENTS

CN 107459543 A * 12/2017

* cited by examiner

*Primary Examiner* — Emily M Le

(74) *Attorney, Agent, or Firm* — Kilyk & Bowersox, P.L.L.C.

(57) ABSTRACT

To extract, from plants such as *freesia*, a novel useful substance which is important in the food/pharmaceutical industry and which is expected to be useful for human health. The present inventors have found that an aromatic compound glycoside, which is a novel substance, is produced in a *freesia* cultivar having yellow petals such as "Ishikawa f2" in the flower thereof. The inventors have further confirmed that the glycoside exhibits an antioxidant effect, a lipid metabolism-improving effect, and a diabetes-ameliorating effect.

20 Claims, 18 Drawing Sheets

Quercetin
(5,7,3',4'-Tetrahydroxyflavonol)

Kaempferol
(5,7,4'-Trihydroxyfavonol)

Caffeic acid

AROMATIC GLYCOSIDE AND METHOD FOR PRODUCING THE GLYCOSIDE

FIELD OF THE INVENTION

The present invention relates to a novel aromatic compound (polyphenol) glycoside (more particularly, a caffeic acid flavonol glycoside ester); to a method for producing the glycoside; and to an antioxidant composition, an antioxidant food composition, a lipid metabolism-improving composition, and a diabetes-prophylactic/ameliorating composition, each composition containing the glycoside.

The present application claims priority to Japanese Patent Application Nos. 2022-63690 and 2022-92106, which are incorporated herein by reference.

BACKGROUND ART

Red, orange, and yellow pigments originating from the fruits of saffron (*Monocotyledoneae, Asparagares, Iridaceae, Crocus sativus*, stigma) and gardenia (*Dicotyledoneae, Gentianales, Rubiaceae, Gardenia jasminoides*) are important in the food industry. These pigments are each formed of an aqueous carotenoid (apocarotenoid) such as a C20 crocetin or crocin (i.e., a derivative formed by esterifying each terminal of crocetin with two glucose molecules) and are used as food additives, functional foods, and pharmaceutical product sources.

Yellow crocus and gardenia (mature flower) also contain crocetin and crocetin glycoside in the petals (see Non-Patent Documents 1 and 2).

*Crocosmia* (*Iridaceae, Crocosmia×crocosmiiflora*) is reported to contain crocin in the orange petals (anthesis: July to September) (Non-Patent Document 3). Notably, the name "*Crocosmia*" means "aroma of saffron" in Latin.

*Freesia* (*Iridaceae, Freesia refracta*) is a flower plant indigenous to the Cape region of South Africa and is also called "Asagisuisen," "Shobusuisen," or "*Kohsetsuran*." Actually, a number of garden cultivars (*Freesia×hybrida*) have been bred. These garden cultivars have various flower colors including white, yellow, orange, red, pink, purple, and blue (anthesis: March to April). Among *freesia* cultivars distributed in Japan, 78% of them are yellow flower cultivars (Non-Patent Document 4). Among yellow *freesia* cultivars, a large-flower cultivar "Aladin" is most widely cultivated in Japan (Non-Patent Document 5). The garden yellow *freesia* cultivars are not limited to the aforementioned cultivars, and there are many other examples, including Porto passat, Gold flame, Kayak, Spring time, Boulevard, and Rapid yellow.

"Airy flora" is a *freesia* cultivar (*Freesia×hybrida*) developed uniquely in Ishikawa Prefecture. A characteristic feature of airy flora resides in a wide variety of colors of flower, and 10 currently distributed cultivars have flower colors that are different from one another. The various flower colors include pale purple, red, pink, orange, yellow, and white. Notably, a cultivar "airy flora-airy yellow (called "Ishikawa f2") is a yellow flower cultivar. The cultivar "Ishikawa f2" has been created in Ishikawa Prefecture through hybridization between a large-flower cultivar "Aladin" and an early maturing cultivar "Rapid yellow" (Non-Patent Document 5).

Previously, the present inventors found that crocetin neapolitanosyl ester (crocetin glycoside; an aqueous apocarotenoid in which three glucose molecules are bonded via an ester bond to one terminal of crocetin) and crocetin di-neapolitanosyl ester (crocetin glycoside; an aqueous apocarotenoid in which three glucose molecules are bonded via an ester bond to both terminals of crocetin) are produced as yellow pigments in the petals of *freesia* having yellow petals (i.e., "Ishikawa f2" or Aladin). That is, the inventors elucidated that the yellow color of yellow *freesia* is attributed to these apocarotenoids (Patent Document 1). Yellow *freesia* is a unique plant which can produce, as a primary ingredient, crocetin neapolitanosyl ester or crocetin di-neapolitanosyl ester. In addition, the present inventors were the first to report isolation of crocetin neapolitanosyl ester from a plant present in the natural world.

A large variety of aromatic compounds exist in the natural world. Examples of low-molecule aromatic compounds (polyphenols) produced by higher plants include flavonoids having a C6-C3-C6 skeleton and phenylpropanoids having a C6-C3 skeleton. Among flavones (i.e., typical flavonoids), a flavone derivative having a hydroxyl group at 3-position is called a flavonol.

Notably, the aforementioned saffron (*Crocus sativus*) is reported to contain, as accessory ingredients, quercetin glycoside and kaempferol glycoside in very small amounts in the flower (Non-Patent Document 6). However, it has never been reported that saffron contains the same ingredient as the aromatic compound glycoside of the present invention.

PRIOR ART DOCUMENTS

Patent Document

[Patent Document 1] Japanese Patent Application Laid-Open (kokai) No. 2021-126053

Non-Patent Documents

[Non-Patent Document 1] A. Rubio Moraga et al., Crocins with High Levels of Sugar Conjugation Contribute to the Yellow Colours of Early-Spring Flowering Crocus Tepals. PLoS ONE 8(9):e71946, 2013. https://doi.org/10.1371/journal.pone.0071946

[Non-Patent Document 2] S. R. Sommano et al., Recovery of crocins from floral tissue of *Gardenia jasminoides* Ellis. Front Nutrition 7: 106, 2020.

[Non-Patent Document 3] Akemi Ohmiya, Diversity of carotenoid composition in flower petals. JARQ 45: 163-171, 2011

[Non-Patent Document 4] Takeshi Motozu, *Freesia* Historical Changes of Breeding, Cultivation Research and Commercial production in Cut *Freesia*, Ibaraki Agricultural Center Research Report 15: 1-31, 2015

[Non-Patent Document 5] Minoru Murahama et al., Breeding of new *freesia* cultivar "Ishikawa f2," Hort. Res. (Japan) 19: 309-311, 2020

[Non-Patent Document 6] P. Vignolini et al, Characterization of by-products of saffron (*Crocus sativus* L.) production. Natural Product Communications 3: 1959-1962, 2008.

SUMMARY OF THE INVENTION

Problems to be Solved by the Invention

An object to be attained by the present invention is to extract, from plants such as *freesia*, a novel useful substance which is important in the food/pharmaceutical industry and which is expected to be useful for human health.

Means for Solving the Problems

The present inventors have conducted extensive studies in order to attain the aforementioned object, and have found that an aromatic compound glycoside (an ester compound formed from caffeic acid and flavonol glycoside), which is a novel substance, is produced in a *freesia* cultivar having yellow petals such as "Ishikawa f2" in the flower thereof. The inventors have further confirmed that the glycoside exhibits an antioxidant effect, a lipid metabolism-improving effect, and a diabetes-prophylactic/ameliorating effect. The present invention has been accomplished on the basis of these findings.

The present invention includes the following.

1. A compound represented by formula (B) or (A):

[F1]

(B)

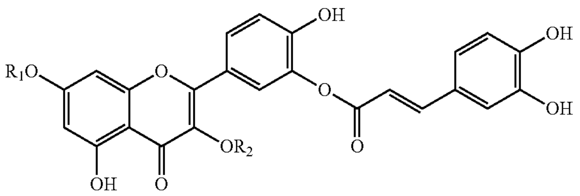

[F2]

(A)

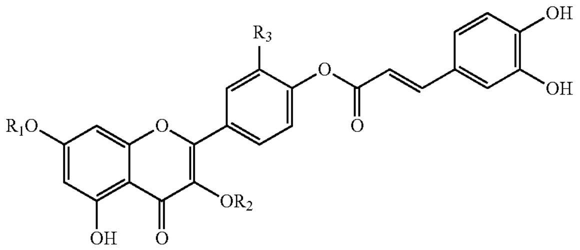

(wherein $R_1$ represents a rhamnose residue, a glucose residue, a glucuronic acid residue, or H; $R_2$ represents a rhamnose residue, a glucose residue, H, a glucose residue-glucose residue, a glucose residue-rhamnose residue, or a rhamnose residue-glucose residue; and $R_3$ in formula (A) represents H or OH).

2. A compound according to 1 above, which is a compound represented by formula (2):

[F3]

(2)

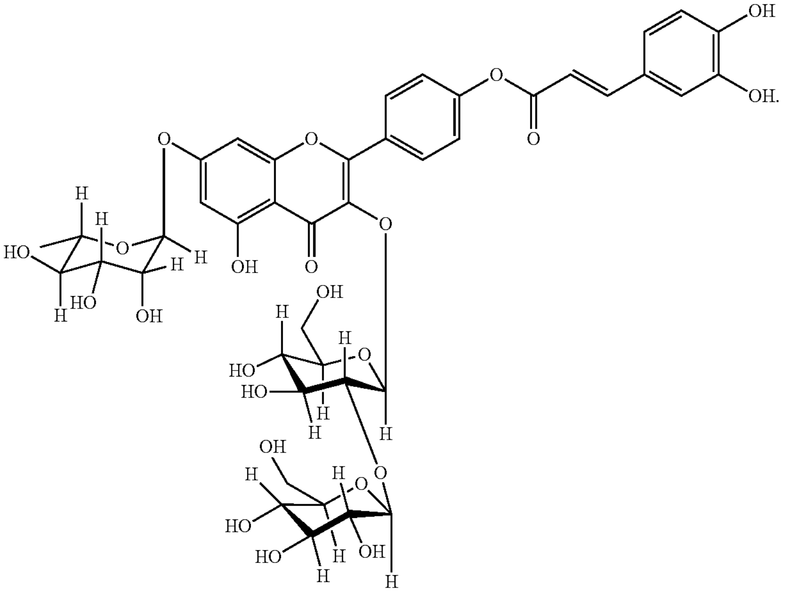

3. A compound according to 1 above, which is a compound represented by formula (6):
[F4]
(6)
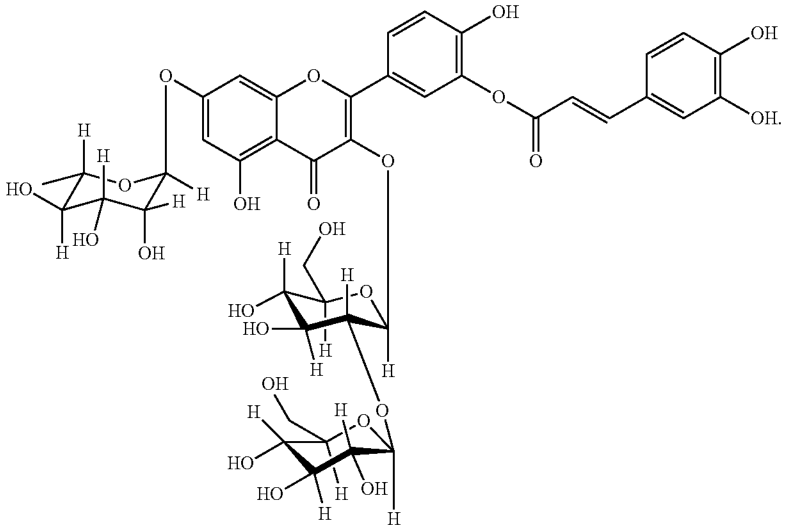
4. A compound according to 1 above, which is a compound represented by formula (7):
[F5]
(7)
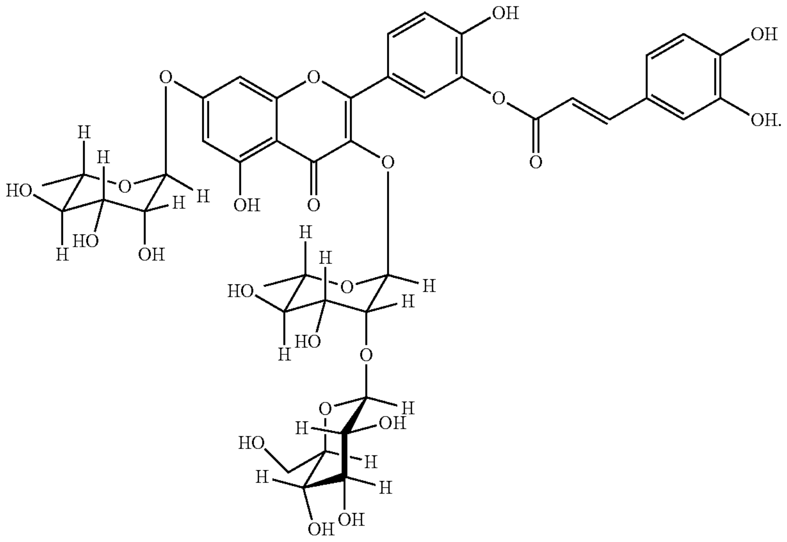

5. A compound according to 1 above, which is a compound represented by formula (8):
[F6]
(8)
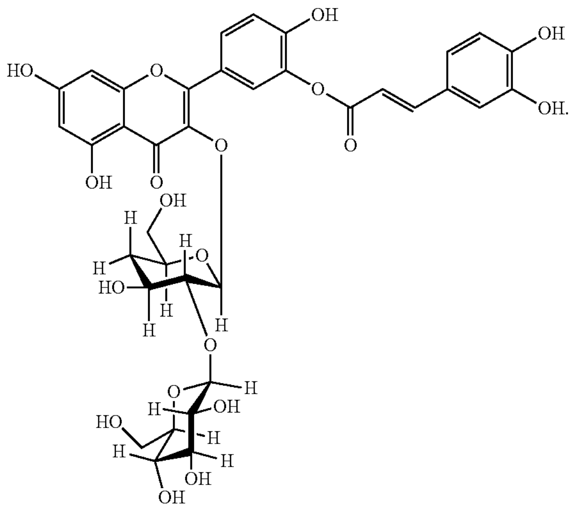
6. A compound according to 1 above, which is a compound represented by formula (9):
[F7]
(9)
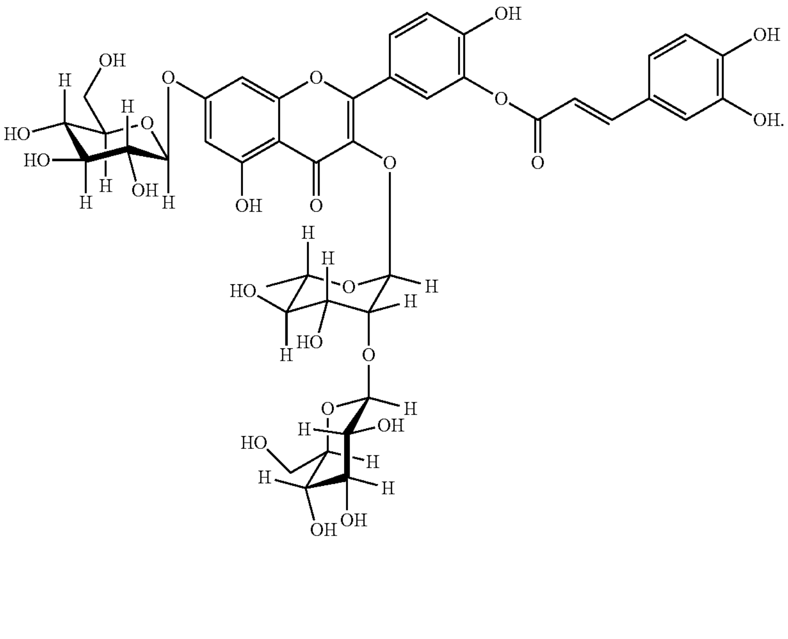

7. A compound according to 1 above, which is a compound represented by formula (1):
[F8]
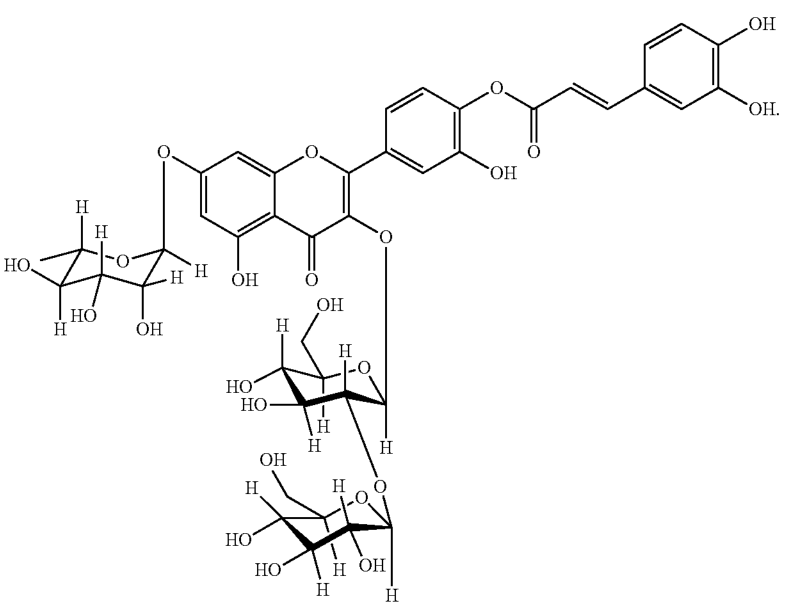
(1)
8. A compound according to 1 above, which is a compound represented by formula (3):
[F9]
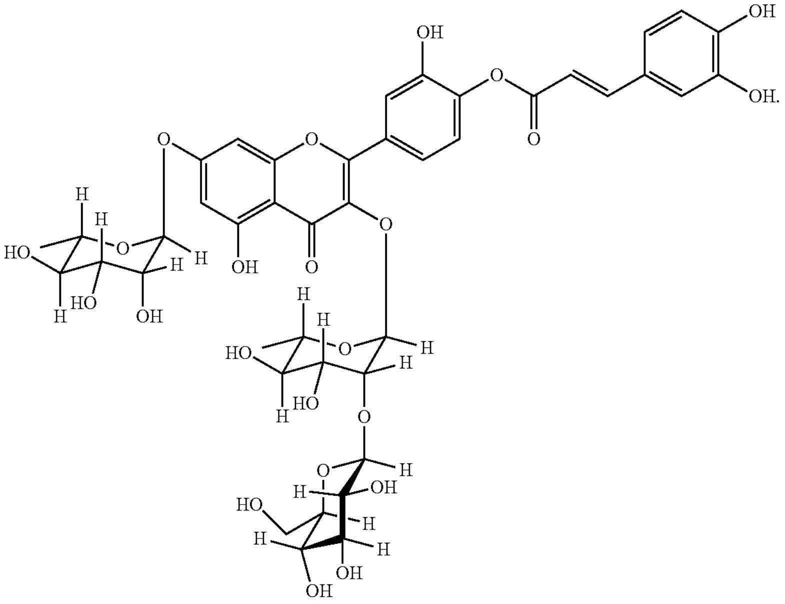
(3)

9. A compound according to 1 above, which is a compound represented by formula (4):
[F10]
(4)
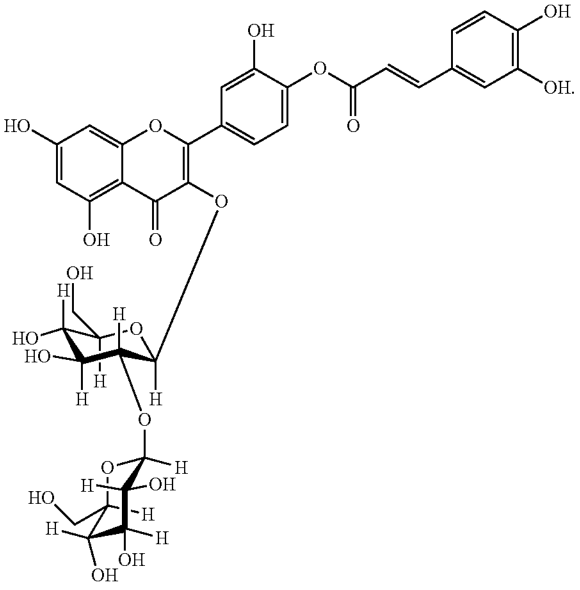
10. A compound according to 1 above, which is a compound represented by formula (5):
[F11]
(5)
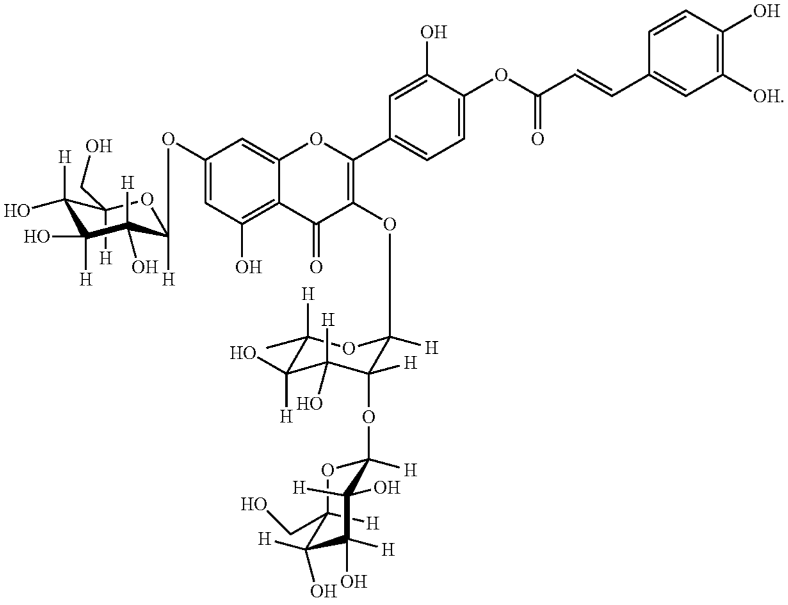

11. A compound according to 1 above, which is a compound represented by formula (10):

[F12]

(10)

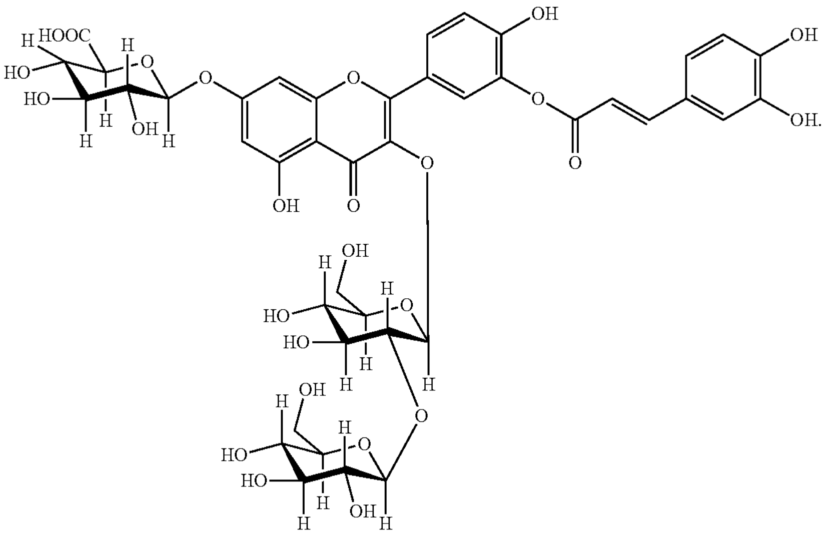

12. A compound according to 1 above, which is a compound represented by formula (11):

[F13]

(11)

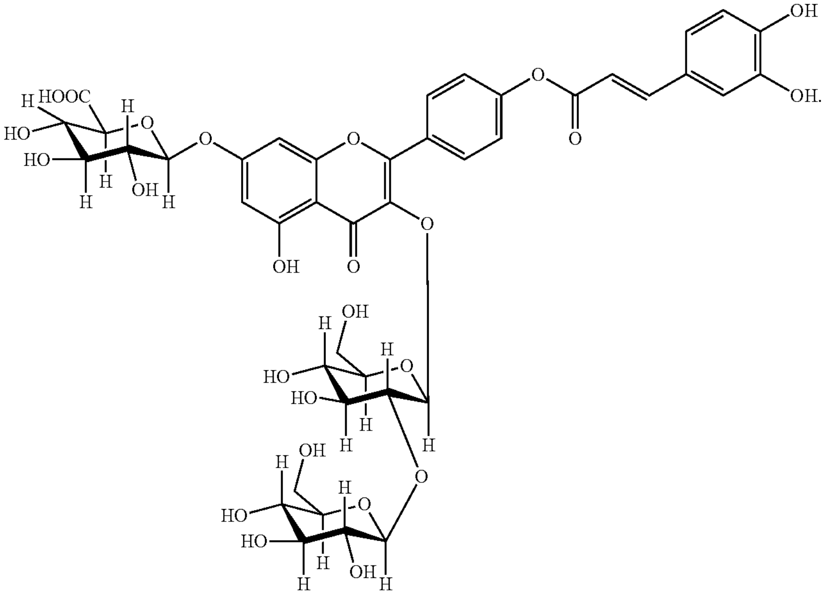

13. An antioxidant composition or an antioxidant food composition, which contains one or more compounds as recited in any of 1 to 12 above.

14. A lipid metabolism-improving composition, a lipid metabolism-improving food composition, a diabetes-prophylactic/ameliorating composition, or a diabetes-prophylactic/ameliorating food composition, which contains one or more compounds as recited in any of 1 to 12 above.

15. A method for producing an aromatic compound glycoside, the method comprising a step of extracting, from a plant which can produce an aromatic compound, one or more compounds as recited in any of 1 to 12 above.

16. A production method according to 15 above, wherein the plant which can produce an aromatic compound is *freesia*.
17. A production method according to 16 above, wherein the *freesia* is yellow *freesia*.
18. A production method according to 17 above, wherein the yellow *freesia* is a cultivar of airy flora-airy yellow (Ishikawa f2), Aladin, Porto passat, Gold flame, Kayak, Spring time, or Boulevard.

Effects of the Invention

The invention can provide a novel aromatic compound glycoside, and an antioxidant composition, a lipid metabolism-improving composition, or a diabetes-prophylactic/ameliorating composition, each containing the glycoside.

MODES FOR CARRYING OUT THE INVENTION

Subject Matters of the Present Invention

The present invention is directed to an aromatic compound glycoside; to a method for producing the glycoside; and to an antioxidant composition, an antioxidant food composition, a lipid metabolism-improving composition, a lipid metabolism-improving food composition, a diabetes-prophylactic/ameliorating composition, and a diabetes-prophylactic/ameliorating food composition, each containing the glycoside.

The present invention will be described in detail.

(Aromatic Compound Glycosides)

The aromatic compound glycoside of the present invention is a compound represented by the following formula (B) or (A):

[F14]

(B)

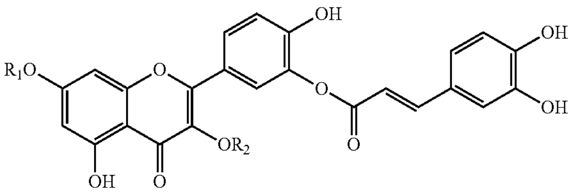

[F15]

(A)

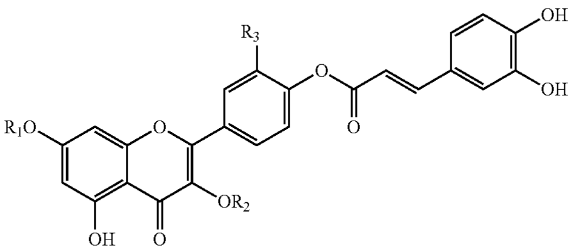

(wherein $R_1$ represents a rhamnose residue, a glucose residue, a glucuronic acid residue, or H; $R_2$ represents a rhamnose residue, a glucose residue, H, a glucose residue-glucose residue, a glucose residue-rhamnose residue, or a rhamnose residue-glucose residue; and $R_3$ represents H or OH).

Figure 12:
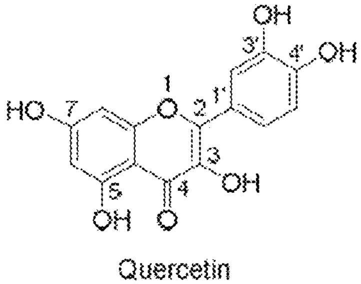
FIG. 12 Structural formulae of quercetin (left in FIG. 12), kaempferol (center in FIG. 12), and caffeic acid (right in FIG. 12).
Figure 12:
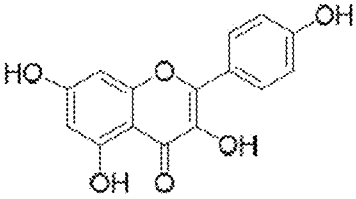
Figure 12:
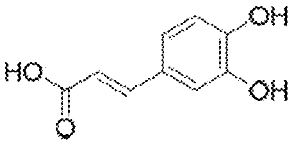

Each of quercetin (left in FIG. 12) and Kaempferol (center in FIG. 12) is a flavonol forming the aromatic compound of the present invention, and caffeic acid (right in FIG. 12) is a carboxylic acid-type phenyl propanoid compound forming the aromatic compound of the present invention.

Compound 1

Compound 1 is an example of the aromatic compound glycoside of the present invention and is represented by the following formula (6):

[F16]
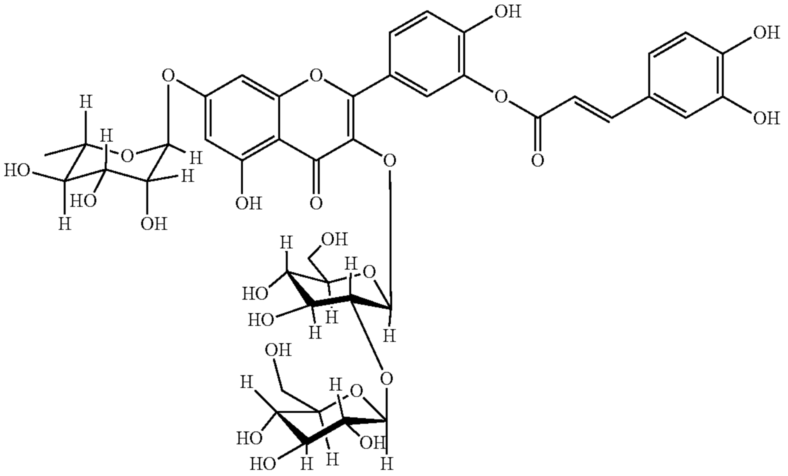
(6)
(see Example 3).
Compound 2
Compound 2 is an example of the aromatic compound glycoside of the present invention and is represented by the following formula (2):
[F17]
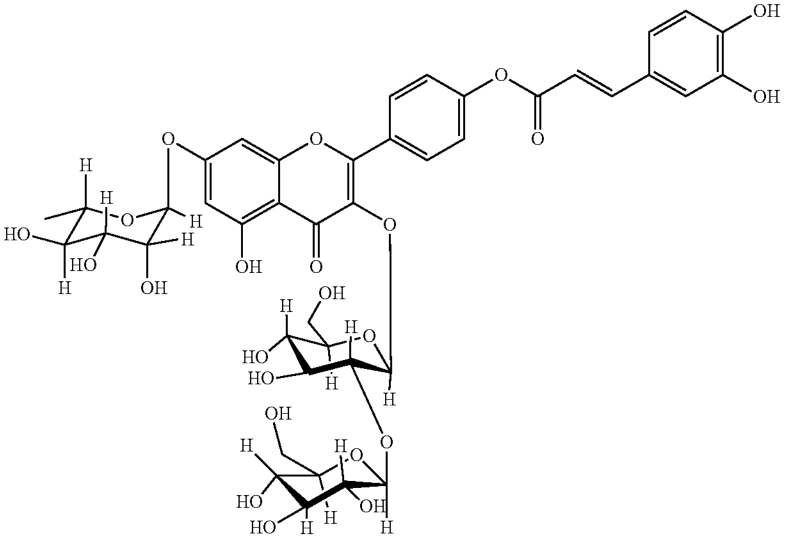
(2)
(see Example 4).
Compound 3
Compound 3 is an example of the aromatic compound glycoside of the present invention and is represented by the following formula (7):

[F18]

(7)

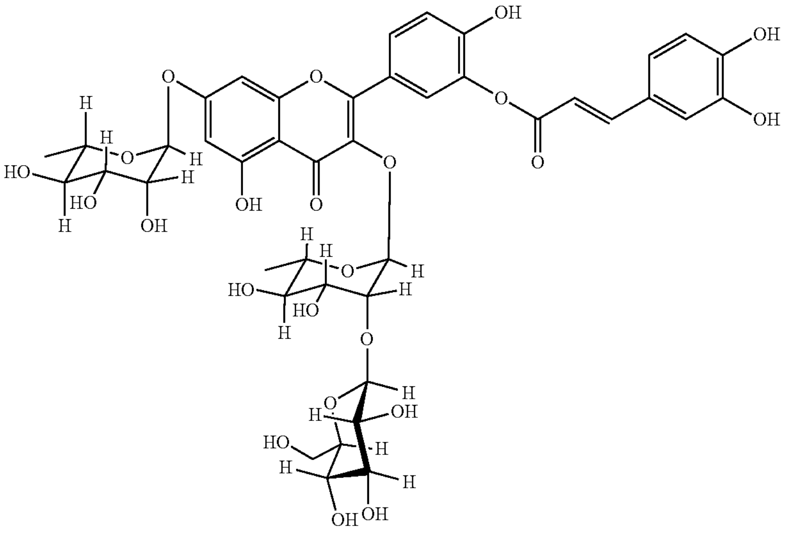

(see Example 5).

Compound 4

Compound 4 is an example of the aromatic compound glycoside of the present invention and is represented by the following formula (8):

[F19]

(8)

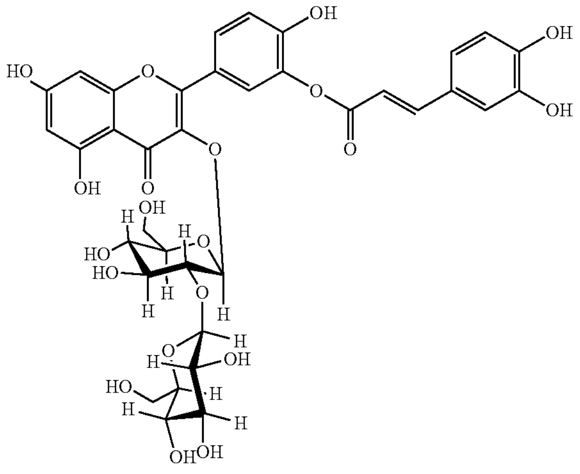

(see Example 6).

Compound 5

Compound 5 is an example of the aromatic compound glycoside of the present invention and is represented by the following formula (9):

[F20]

(9)

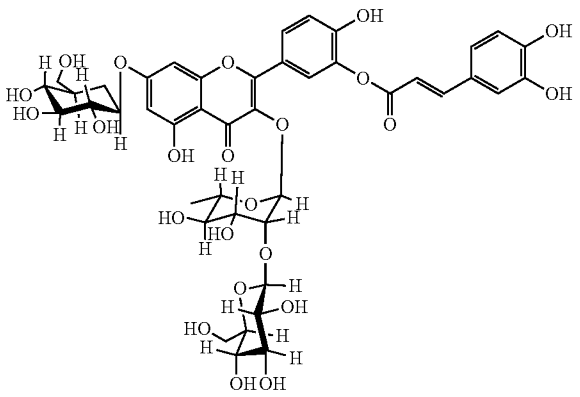

(see Example 7).

Compound 20

Compound 20 is an example of the aromatic compound glycoside of the present invention and is represented by the following formula (10):

[F21]

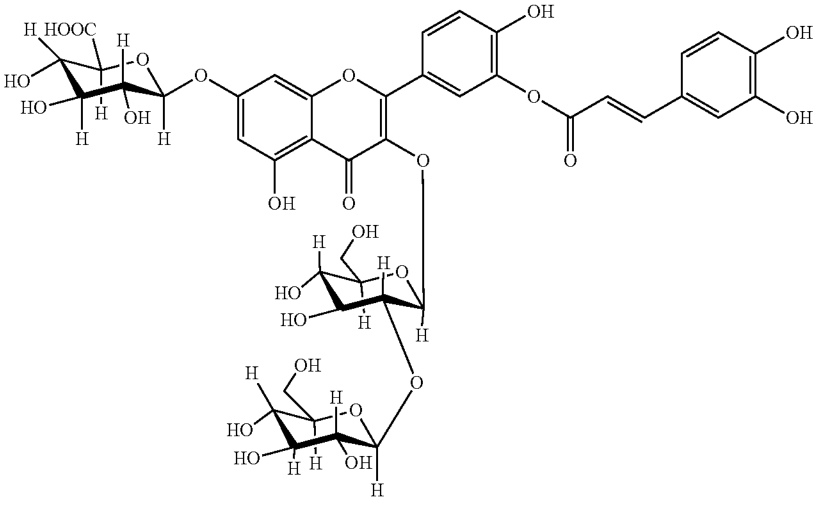

(10)

(see Example 12).

Compound 21

Compound 21 is an example of the aromatic compound glycoside of the present invention and is represented by the following formula (11):

[F22]

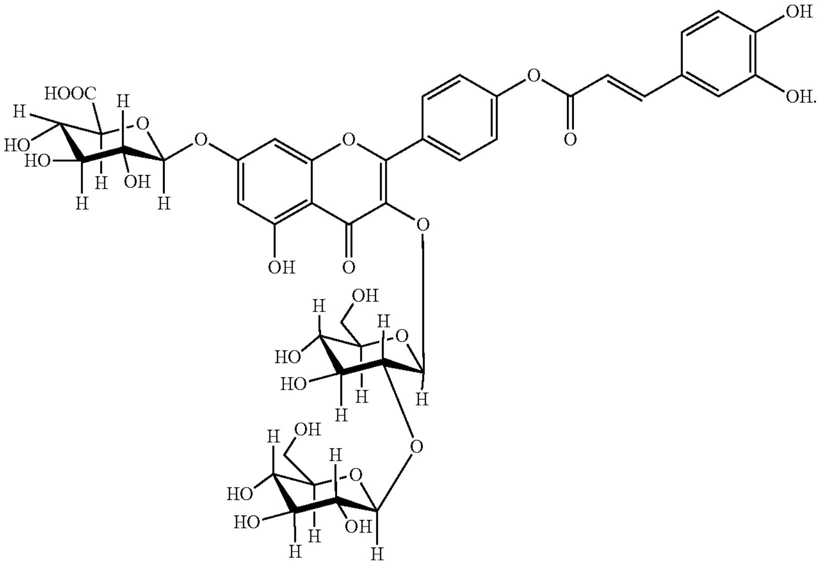

(11)

(see Example 13).

(Embodiments of the Antioxidant Composition or the Antioxidant Food Composition)

The antioxidant composition or antioxidant food composition according to the present invention contains any one or more members of a compound represented by formula (A) or (B) and compounds 1 to 11.

Alternatively, the antioxidant composition of the present invention may be incorporated into another pharmaceutical agent (e.g., an anti-cancer agent).

The antioxidant food composition of the present invention may be formulated into a food product. More specifically, the antioxidant food composition of the present invention may be formulated into the following products: supplements, cooked rice, noodles, bread, cereal, vegetables, meats, processed foods, confectionery, milk, refreshing beverages, alcoholic beverages, jelly, chewing gum, tablets, nutritional supplementary foods, food additives, etc. Notably, such food products include functional foods, health foods, and health directive foods.

(Ingredients of the Antioxidant Composition or Antioxidant Food Composition)

The antioxidant composition or antioxidant food composition according to the present invention may further contain an additional ingredient. No particular limitation is imposed on the "additional ingredient," so long as it is acceptable in food products and pharmaceutical agents. Examples of the additional ingredient include ingredients of interest for forming the target food product, an oily ingredient, a vehicle, a disintegrator, a binder, a lubricant, a coating agent, a colorant, a color developer, a corrigent, a flavor, an antioxidant, an antiseptic, a taste improver, an acidulant, a sweetener, a fortifier, a vitamin, a leavening agent, a thickener, and a surfactant. According to the form of the composition of the present invention, appropriate ingredients may be selected and may be used in combination.

(Lipid Metabolism-Improving Composition, Lipid Metabolism-Improving Food Composition, Diabetes-Prophylactic/Ameliorating Composition, and Diabetes-Prophylactic/Ameliorating Food Composition)

Each of the Lipid metabolism-improving composition, lipid metabolism-improving food composition, diabetes-prophylactic/ameliorating composition, and diabetes-prophylactic/ameliorating food composition of the present invention contains any one or more members of a compound represented by formula (A) or (B) and compounds 1 to 11.

Alternatively, any of the compositions of the present invention may be incorporated into another pharmaceutical agent (e.g., an anti-cancer agent).

Any of the compositions of the present invention may be formulated into a food product. More specifically, the composition of the present invention may be formulated into the following products: supplements, cooked rice, noodles, bread, cereal, vegetables, meats, processed foods, confectionery, milk, refreshing beverages, alcoholic beverages, jelly, chewing gum, tablets, nutritional supplementary foods, food additives, etc. Notably, such food products include functional foods, health foods, and health directive foods. Furthermore, the aforementioned composition of the present invention may also be employed as a lipid metabolism-improving agent, or a diabetes-prophylactic/ameliorating agent.

(Agent of the Present Invention)

The agent of the present invention is used to suppress or retard the onset of a disease. Such prophylactic effects include prevention of the onset of a disease and prevention of recurrence of the disease after the treatment thereof. The agent of the present invention is used to cure a disease, improve symptom(s), and suppress progress of the symptom (s).

The target to which the agent of the present invention is administered is preferably a mammal. As used herein, the term "mammal" refers to a warm-blooded vertebrate. Examples the vertebrate include primates such as humans and monkeys; rodents such as mice, rats, and rabbits; pets such as dogs and cats; and domestic animals such as cows, horses, and pigs. The agent of the present invention is preferably administered to a primate, particularly to a human.

(Carrier)

The agent of the present invention contains, in addition to the aromatic compound glycoside of the present invention, one or more carriers which are pharmaceutically acceptable. Generally, the term "pharmaceutically acceptable carrier" refers to a carrier which is unreactive with the active ingredient(s) of the present invention. Examples of the carrier include an extender, a diluent, an encapsulating agent, etc., which are inert or non-toxic, or solid or liquid. Specific examples include water, ethanol, polyol (e.g., glycerol, propylene glycol, or liquid polyethylene glycol), appropriate mixtures thereof, and a solvent or dispersion medium such as vegetable oil.

(Embodiments of the Agent of the Present Invention)

The agent of the present invention may be administered perorally or parenterally. Examples of the administration route include percutaneous administration, subcutaneous administration, transmucosal administration, intravenous administration, intraarterial administration, intramuscular administration, intraperitoneal administration, vaginal administration, transpulmonary administration, intracerebral administration, intraocular administration, and intranasal administration. Examples of the peroral preparation include tablet, granule, fine granule, powder, capsule, chewable agent, pellet, syrup, liquid, suspension, and inhalation. Examples of the parenteral preparation include suppository, retention-type enema, intravenous drip, eye drop, nasal drop, pessary, injection, and mouth wash, and external skin preparations such as ointment, cream, gel, controlled-release patch agent, and plaster. Alternatively, the agent of the present invention may be administered parenterally by the mediation of a sustained-release subcutaneous implant or a target delivery system (e.g., monoclonal antibody, vector delivery, ion implantation, polymer matrix, liposome, or microsphere).

(Additive)

The agent of the present invention may further contain an additive which is generally used in the pharmaceutical field. Examples of such an additive include a vehicle, a binder, a disintegrator, a lubricant, an antioxidant, a colorant, and a corrigent. These additives may be used in accordance with needs.

(Aromatic Compound Glycoside Production Method)

The method of the present invention for producing the aromatic compound glycoside may be based on extraction of a useful compound (in particular, a water-soluble low-molecule compound) from a plant which can produce an aromatic compound. For example, the following procedure may be employed.

A whole or part of a plant which can produce an aromatic compound (preferably, flowers of *freesia*) is collected. If necessary, the plant material is lyophilized, air-dired, or dried with heating. The raw material or dried product is pulverized and then subjected to solvent extraction, to thereby yield an aromatic compound glycoside of interest.

Examples of the extraction solvent which may be used in the invention include water; alcohols such as methanol, ethanol, propanol, and butanol; glycols such as 1,3-butylene glycol, glycerin, such as propylene glycol; esters such as ethyl acetate and butyl acetate; ethers such as ethyl ether, propyl ether, isopropyl ether, tetrahydrofuran, and dioxane; halohydrocarbons such as dichloromethane, methylene chloride, and chloroform; polar organic solvents such as acetone; and non-polar organic solvents such as hexane, cyclohexane, and petroleum ether. These solvents may be used singly or in combination of two or more species. Examples of preferred extraction solvents include a dichloromethane-methanol solvent mixture, methanol, and water-containing methanol.

If required, the extract obtained through the aforementioned procedure may be fractionated by use of an organic solvent (e.g., butanol, chloroform, ethyl acetate, toluene, hexane, or benzene) and a highly polar solvent which is immiscible with the organic solvent (e.g., water or water-containing methanol), whereby an active fraction (e.g., an aqueous layer fraction) can be isolated and roughly purified.

If needed, the thus-obtained crude product may be further purified through appropriate separation/purification means such as alumina column chromatography, silica gel chromatography, gel filtration chromatography, ion-exchange chromatography, hydrophobic chromatography, or high-performance liquid chromatography. These separation/purification means may be employed singly or in combination of two or more means for purification.

Alternatively, the aromatic compound glycoside of the present invention may be obtained by collecting a part of a plant which can produce an aromatic compound (e.g., flowers of *freesia*), breaking, centrifuging the broken product with water or the aforementioned solvent added thereto, and recovering the supernatant. The procedure is repeatedly carried out two or more times.

In one embodiment of the method of the present invention for producing the aromatic compound glycoside, *freesia* "Ishikawa F2" is cultivated through forcing or a customary method in a greenhouse. After flowering, flowers of *freesia* "Ishikawa f2" are subsequently picked, and the picked flowers are cryopreserved in a freezer at −80° C. When a considerable amount of frozen flowers have been stocked, the flowers are lyophilized for 3 days. Alternatively, the flowers picked out are dried in air-dried in a dry room for 1 month or longer.

The thus-dried flower is pulverized by means of a mixer, and the resultant powder is washed with dichloromethane ($CH_2Cl_2$)-methanol (MeOH) (1:1), and 100% MeOH is added to the residue, whereby a substance of interest assuming slight yellow is collected via solvent extraction. The extract is concentrated to a small volume, and the concentrate is bi-separated with ethyl acetate (EtOAc)/$H_2O$. Since the target substance is distributed to the aqueous phase, EtOAc is removed so that the volume of the aqueous phase is concentrated to an about half the original volume. The concentrated product is caused to pass through an HP20 column. The HP20 column is washed with water and 50% MeOH, and then the target substance is eluted with 100% MeOH.

The eluted product is concentrated and dried, and the dried product is subjected to reverse phase (C30) preparative HPLC [eluent: 30% acetonitrile ($CH_3CN$)+0.1% trifluoroacetic acid (TFA)], whereby a pure product of the aromatic compound glycoside is isolated as a target substance.

(Identification of Aromatic Compound Glycoside)

In accordance with needs, the thus-obtained pure product is subjected to NMR ($^1H$, $^{13}C$ DQF COSY, HMBC, HMQC, or NOESY) analysis or HRESI-MS (e.g., $(M+Na)^+$).

Subsequently, the product is hydrolized with 2N HCl into aglycone and sugar. The aglycone and sugar are respectively purified through bi-phase separation with EtOAc/$H_2O$ (EtOAc layer: algycone, aqueous layer:sugar).

If required, the aglycone is analyzed through any of various NMR analyses, and the sugar is subjected to optical rotation measurement and $^1H$-NMR analysis. As a result, whether or not the obtained compound is identified to the aromatic compound glycoside of the present invention can be determined.

(Plant Producing Aromatic Compound)

No particular limitation is imposed on the plant which can produce the aromatic compound glycoside of the present invention, so long as the plant can produce the aromatic compound of the present invention. Examples of the plant include plants of the Iridaceae family (e.g., *freesia*), plants of the Rubiacea family, and the plants of Papaveraceae. Among them, *freesia* and yellow-flower plants are preferred, with yellow *freesia* being more preferred.

Examples of yellow *freesia* include Aladin, airy flora-airy yellow (Ishikawa f2), Aladin, Porto passat, Gold flame, Kayak, Spring time, and Boulevard.

The present invention will next be described in detail by way of specific examples, which should not be construed as limiting the invention thereto.

Example 1

(Extraction of Aromatic Compound Glycosides from *Freesia*)

As a yellow-flower variety of *freesia* (*Freesia*×*hybrida*), we used cultivar 'Airy-Flora' 'Airy-Yellow', i.e., 'Ishikawa f2 go' ('f2'), one of the original varieties of Ishikawa Prefecture. The *freesia* 'f2' plants were grown with general conditions in green houses of Ishikawa Agriculture and Forestry Research Center, and their florescent flowers were harvested to use. Furthermore, *freesia* cultivars 'Aladin', 'Passat', 'Goldflame', 'Kayak', 'Spring Time', and 'Boulevard', which are horticulture varieties with yellow petals, were also ordinarily cultivated in green houses of Ishikawa Agriculture and Forestry Research Center.

Copious amounts (1.5 kg) of the 'f2' flowers (whole flowers containing petals, sepals, stamens, and pistils) were harvested in the middle of April. The collected flowers were dried for 2 months indoor at room temperature, while for the ¼-⅓ period we utilized a dehumidification machine (IRIS Ohyama efeel; compressor type) to generate dry flowers with approximately 1/10 weight compared to that of the raw flowers. The dried *freesia* flowers (66.7 g) were powdered by mill for one min, and extracted by adding $CH_2Cl_2$ (dichloromethane)-MeOH (methanol) (1:1) (1 L) and by stirring for 30 min at room temperature in dim light, and then filtrated under reduced pressure.

Next, MeOH (1 L) was added to the filtrated debris, and extracted in the same manner, followed by the vacuum filtration. Further, 80% (V/V) MeOH (1 L) and 50% (V/V) MeOH (1 L) were added to the debris and treated same in a stepwise manner.

As the result of the extraction above, the last debris became nearly white color, since pigments contained in the flowers were totally extracted.

Figure 1:
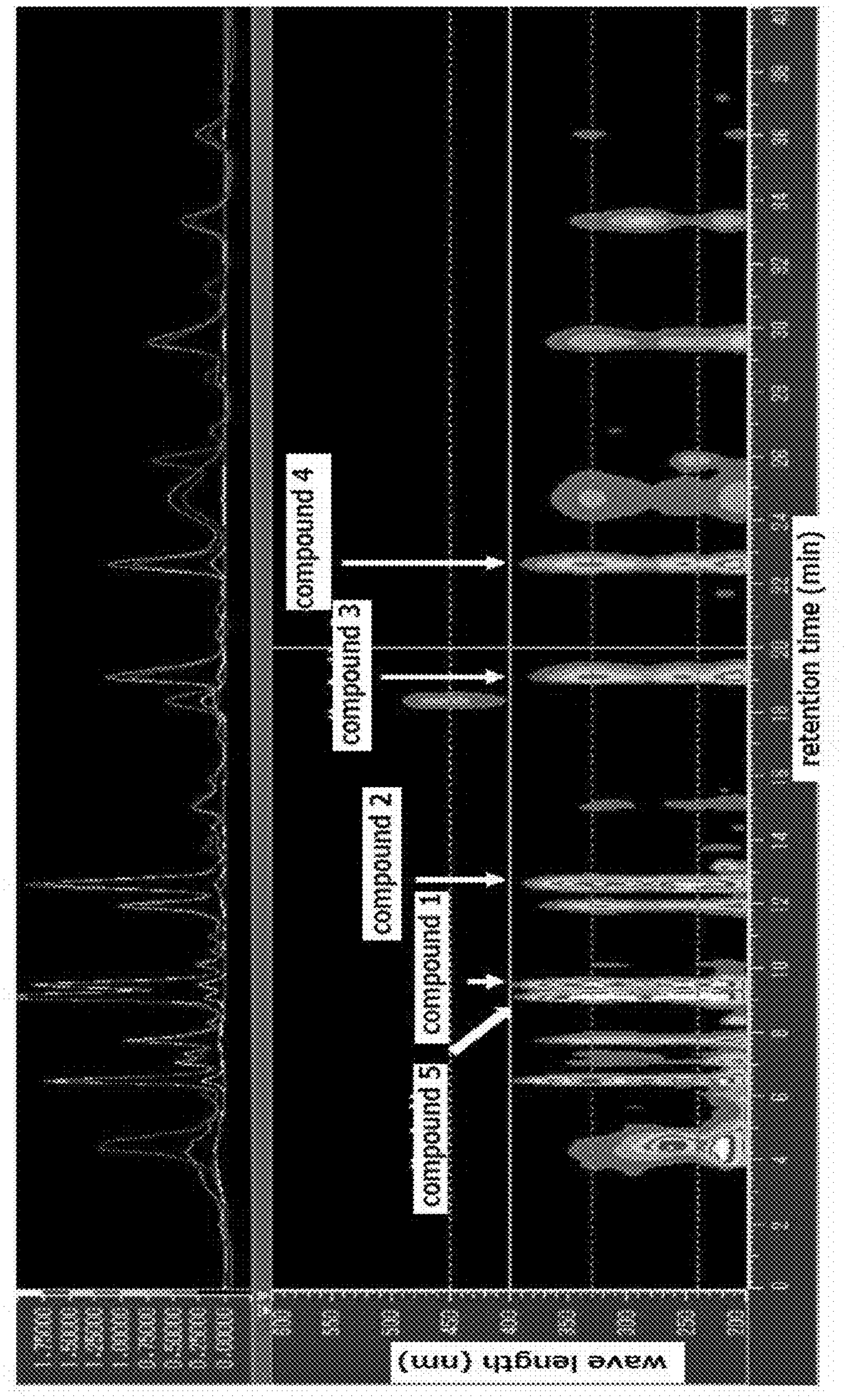
FIG. 1 HPLC analytical results of a *freesia* flower methanol (MeOH) extract [containing aromatic compound glycosides of the present invention].

Thirty pL of each extract was analyzed by HPLC with conditions described as follows. As the results of these HPLC analyses, we confirmed that there are a wide variety of flavonoid (aromatic compound (polyphenol)) glycosides, which were present only in the MeOH extract, as shown in FIG. 1.

Column: CAPCELL PAK ADME (OSAKA SODA) 10 m×250 mm

Solvent: 20% (V/V) $CH_3CN$ (acetonitrile) containing 0.1% (V/V) TFA (trifluoroacetic acid)

Flow rate: 3.0 mL/min

Detection: DAD (diode array detector) 200-600 nm.

As for *freesia* cultivars 'Aladin', 'Passat', 'Goldflame', 'Kayak', 'Spring Time', and 'Boulevard', the petals from the raw flowers (1.5-3 g each) were extracted with MeOH similarly, and analyzed by HPLC. Consequently, these *free-*

*sia* cultivars were confirmed to contain a great variety of flavonoid glycosides, which is similar to the case of 'Ishikawa f2 go'.

Example 2

(Isolation and Purification of Aromatic Compound Glycosides of the Present Invention)

The MeOH extract of 'Ishikawa f2 go' was concentrated to dryness (18.3 g). Main flavonoid glycosides were isolated by preparative HPLC using the conditions described in EXAMPLE 1 and concentrated to dryness, i.e., compound 1 (40.5 mg, RT (retention time) 9.4 min), compound 2 (37.5 mg, RT 12.6 min), compound 3 (43.5 mg, RT 19.2 min), compound 4 (25.5 mg, RT 22.3 min), and compound 5 (43.1 mg, RT 9.1 min) were obtained as the pure compounds. In addition to these five compounds, several flavonoid glycosides further existed in the MeOH extract (FIG. 1).

Example 3

(Structural Determination of Compound 1)

Compound 1 (purified), obtained in EXAMPLE 2, was dissolved in MeOH (0.1 mg/mL) and analyzed by HRESI-MS (+). As a result, the $(M+Na)^+$ ion peak was observed at m/z 957.2294, and the molecular formula of compound 1 was determined as $C_{42}H_{46}O_{24}$ ($C_{42}H_{46}O_{24}Na$, calcd. for 957.2268 (D 2.72 ppm)).

Figure 2:
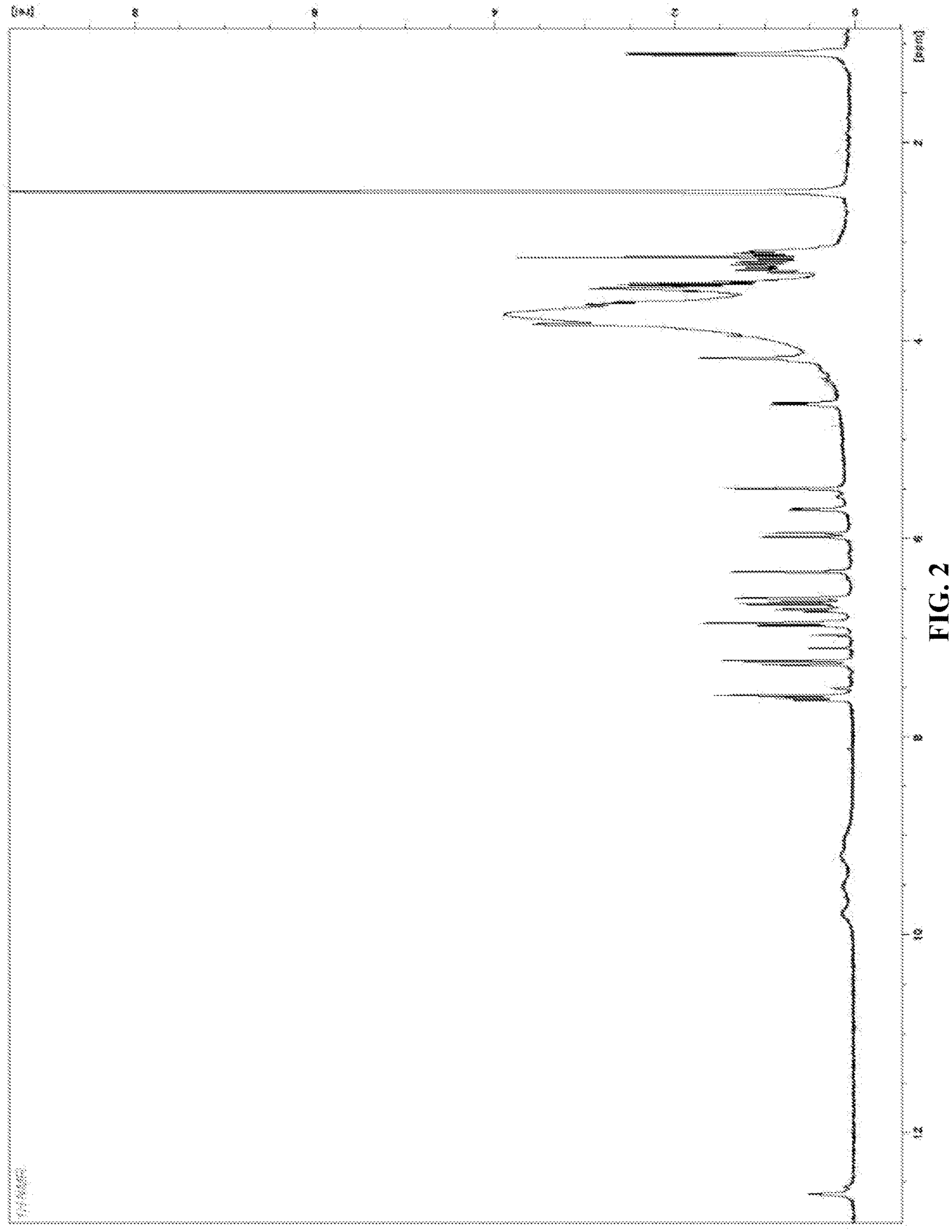
FIG. 2 $^1$H-NMR spectrum (in DMSO-$d_6$) of compound 1.
Figure 3:
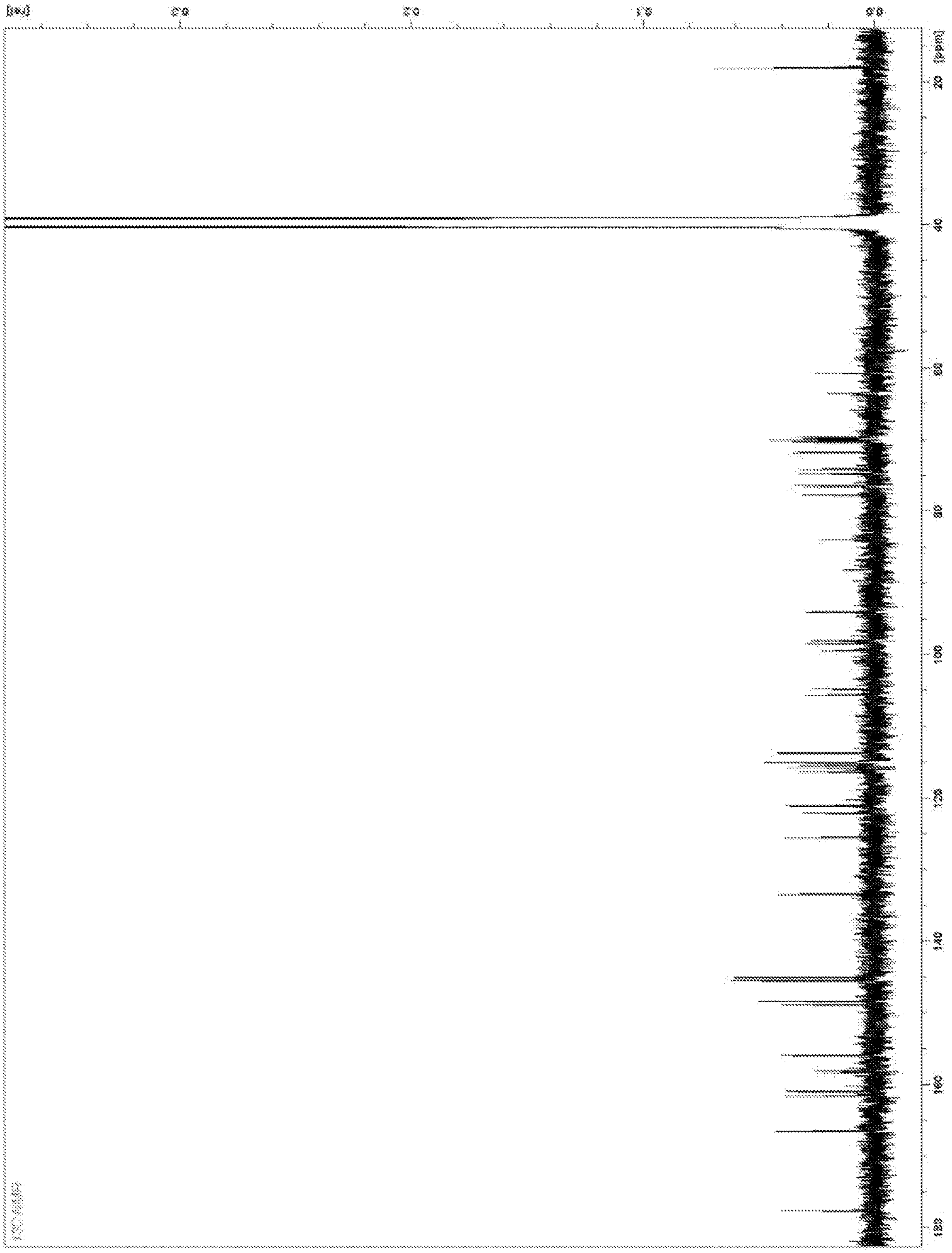
FIG. 3 $^{13}$C-NMR spectrum (in DMSO-$d_6$) of compound 1.

Compound 1 (10 mg) was dissolved in DMSO-$d_6$ (1 mL), and analyzed by 1D NMR (FIG. 2) and $^{13}C$ NMR (FIG. 3)) and 2D ($^1H$-$^1H$ DQF COSY, HMQC, HMBC, NOESY, TOCSY, and J-resolved HSQC). Through analyses of these spectra, the structure of compound 1 was determined as that shown in FORMULA (6).

Compound 1 composes $R_1$=rhamnose residue and $R_2$=glucose residue-glucose residue in GENERAL FORMULA (B), and was confirmed to be a novel compound.

[F23]

(6)

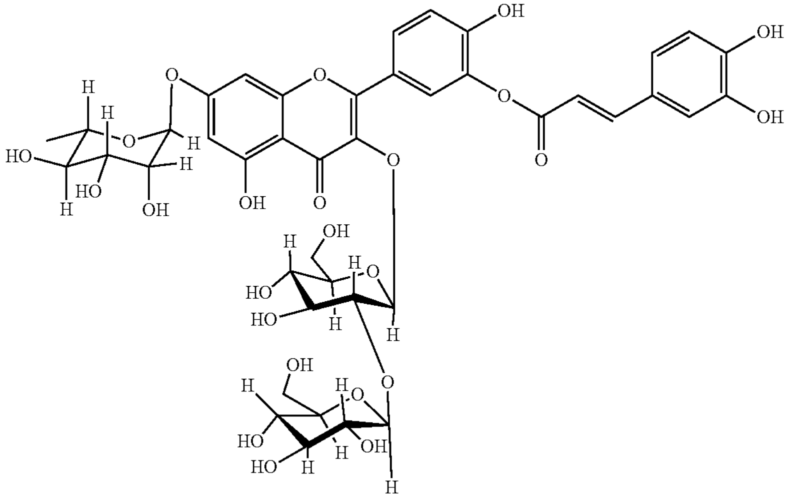

As shown in EXAMPLE 4, caffeic acid in compound 2 was esterified at C-4' of flavonol. Considering the reaction specificity of the esterification enzyme, there should be present at least a trace amount of the compound represented by FORMULA (1), which composes $R_1$=rhamnose residue, $R_2$=glucose residue-glucose residue, and $R_3$=OH in GENERAL FORMULA (A), and was confirmed to be a new compound.

[F24]

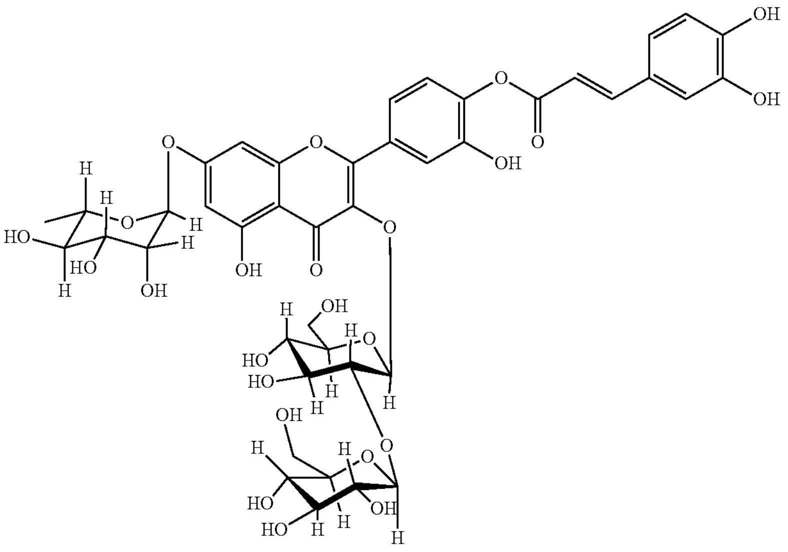

(1)

Example 4

(Structural Determination of Compound 2)

Compound 2 (purified), obtained in EXAMPLE 2, was dissolved in MeOH (0.1 mg/mL) and analyzed by HRESI-MS (+). As a result, the $(M+Na)^+$ ion peak was observed at m/z 941.2354, and the molecular formula of compound 2 was determined as $C_{42}H_{46}O_{23}$ ($C_{42}H_{46}O_{23}Na$, calcd. for 941.2328 (D 2.76 ppm)).

Figure 4:
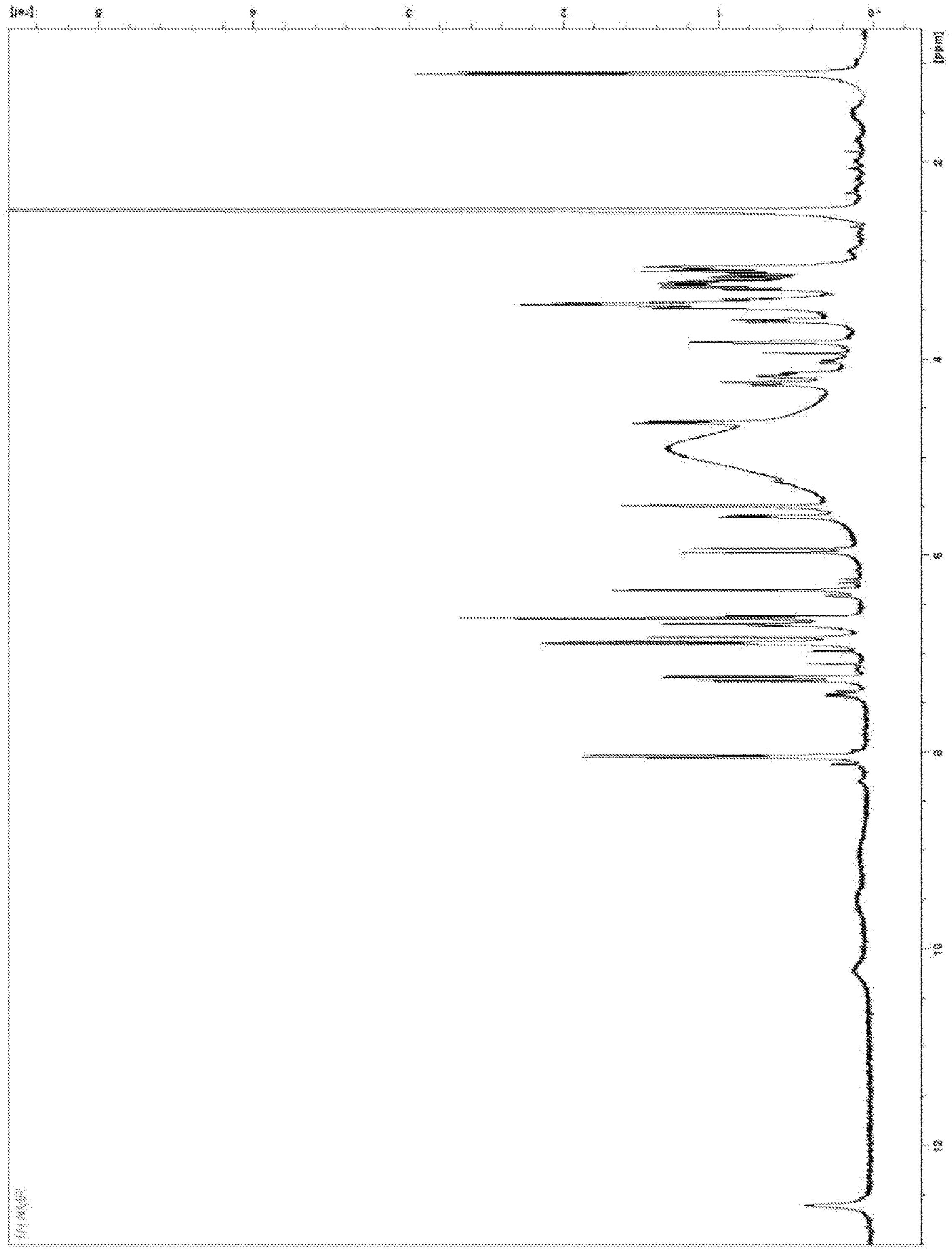
FIG. 4 $^1$H-NMR spectrum (in DMSO-$d_6$) of compound 2.
Figure 5:
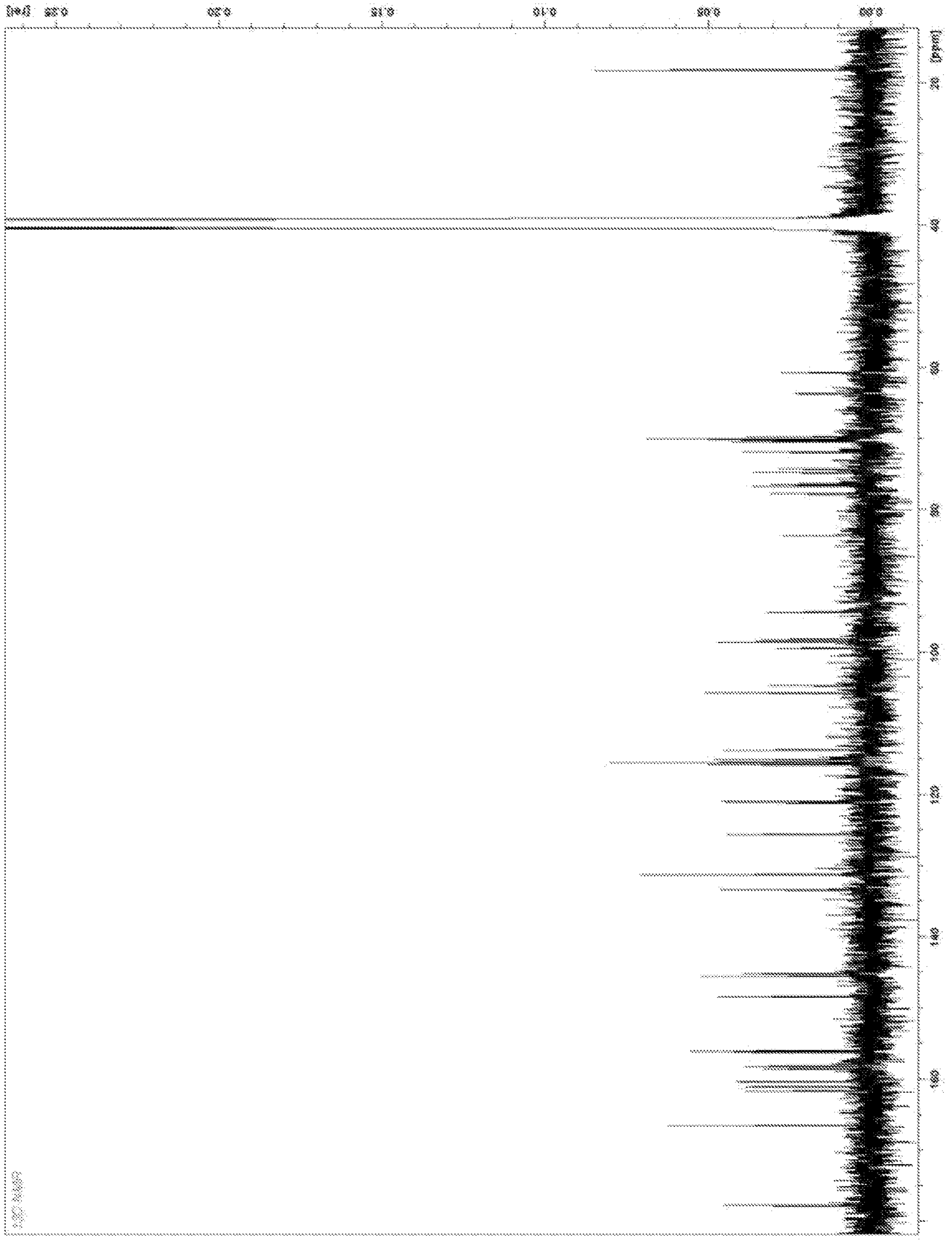
FIG. 5 $^{13}$C-NMR spectrum (in DMSO-$d_6$) of compound 2.

Compound 1 (10 mg) was dissolved in DMSO-$d_6$ (1 mL), and analyzed by 1D ($^1H$ NMR (FIG. 4) and $^{13}C$ NMR (FIG. 5)) and 2D ($^1H$-$^1H$ DQF COSY, HMQC, HMBC, NOESY, TOCSY, and J-resolved HSQC).

Through analyses of these spectra, the structure of compound 2 was determined as that shown in FORMULA (2).

Compound 2 composes $R_1$=rhamnose residue, $R_2$=glucose residue-glucose residue, and $R_3$=H in GENERAL FORMULA (A), and was confirmed to be a novel compound.

[F25]

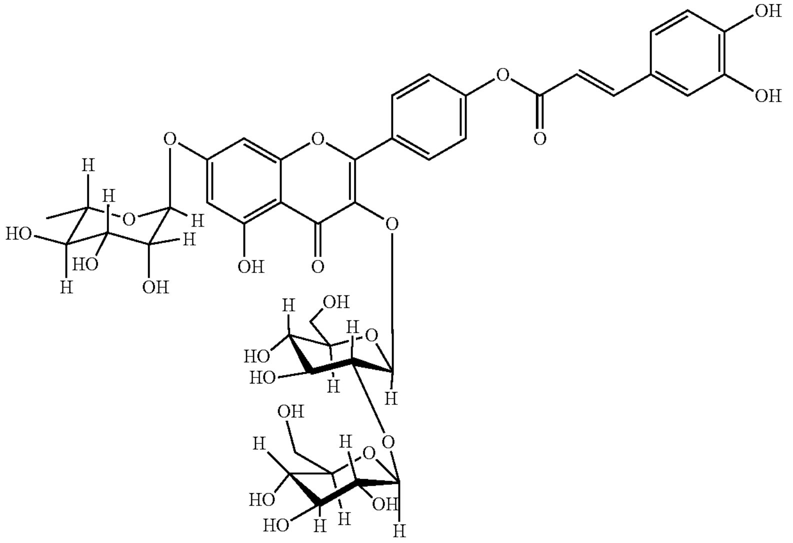

(2)

Example 5

(Structural Determination of Compound 3)

Compound 3 (purified), obtained in EXAMPLE 2, was dissolved in MeOH (0.1 mg/mL) and analyzed by HRESI-MS (+). As a result, the $(M+Na)^+$ ion peak was observed at m/z 941.2371, and the molecular formula of compound 3 was determined as $C_{42}H_{46}O_{23}$ ($C_{42}H_{46}O_{23}Na$, calcd. for 941.2328 (D 4.57 ppm)).

Figure 6:
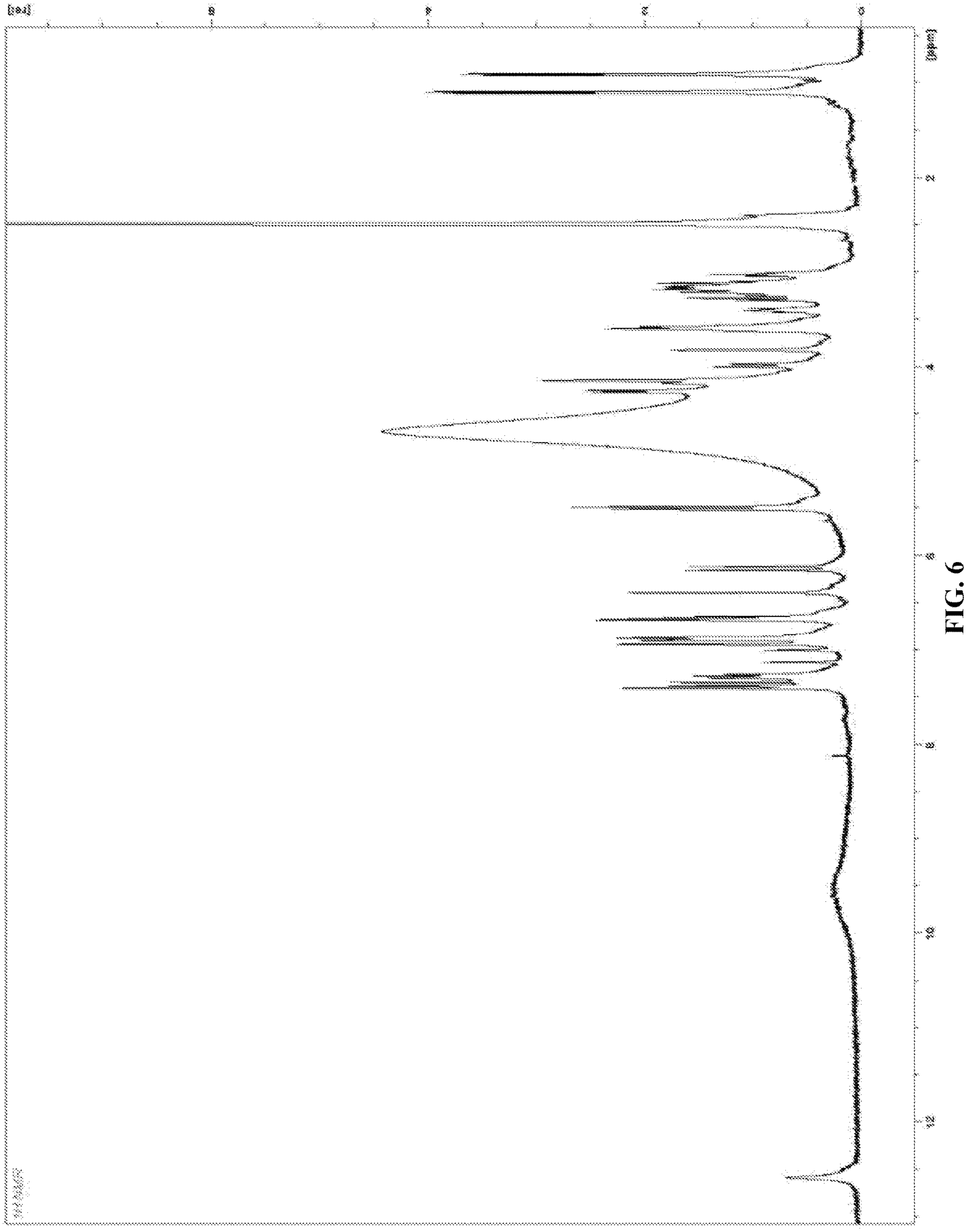
FIG. 6 $^1$H-NMR spectrum (in DMSO-$d_6$) of compound 3.
Figure 7:
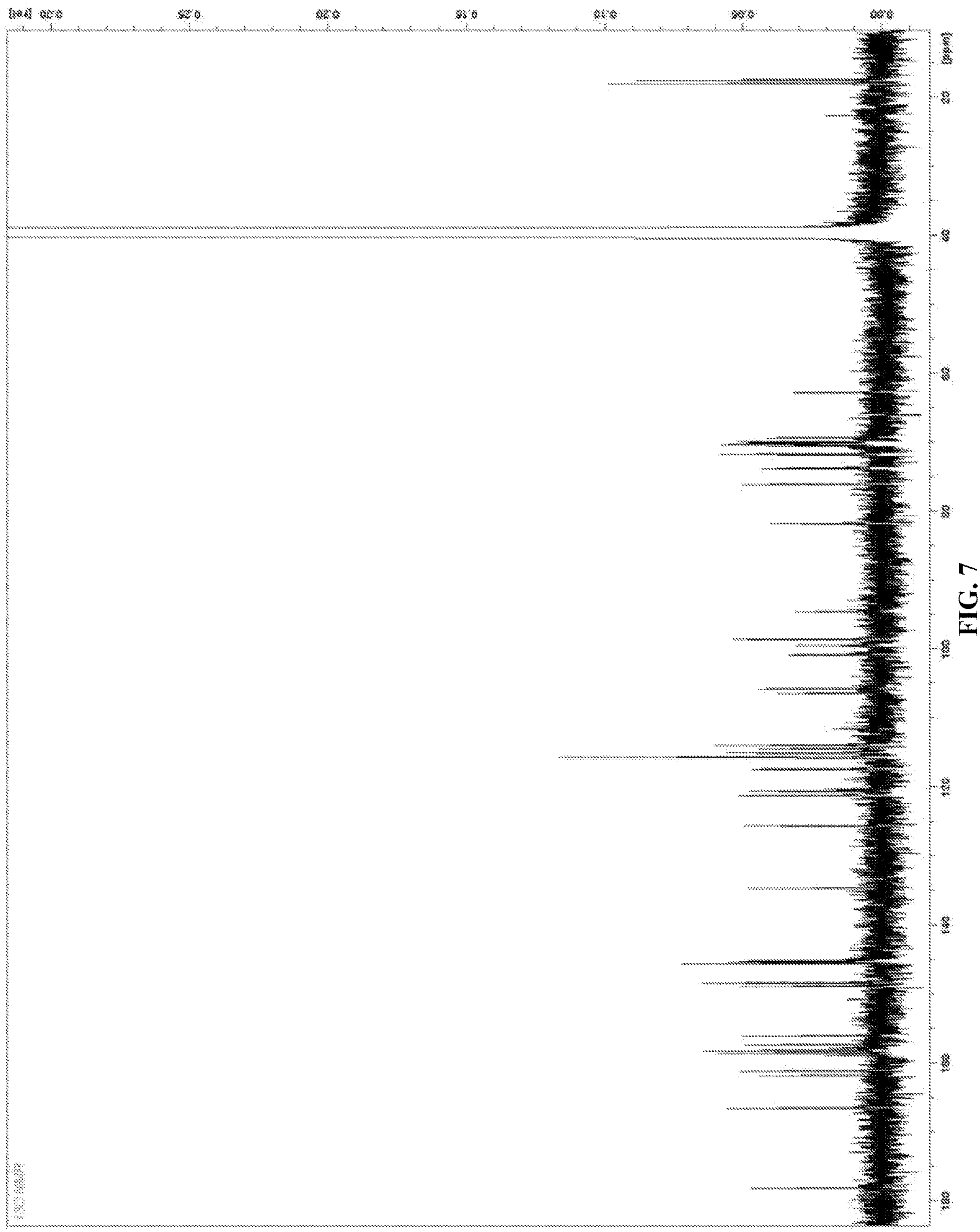
FIG. 7 $^{13}$C-NMR spectrum (in DMSO-$d_6$) of compound 3.

Compound 3 (10 mg) was dissolved in DMSO-$d_6$ (1 mL), and analyzed by 1D ($^1$H NMR (FIG. 6) and $^{13}$C NMR (FIG. 7)) and 2D ($^1$H-$^1$H DQF COSY, HMQC, HMBC, NOESY, TOCSY, and J-resolved HSQC).

Through analyses of these spectra, the structure of compound 3 was determined as that shown in FORMULA (7).

Compound 3 composes $R_1$=rhamnose residue and $R_2$=glucose residue-rhamnose residue in GENERAL FORMULA (B), and was confirmed to be a novel compound.

[F26]

(7)

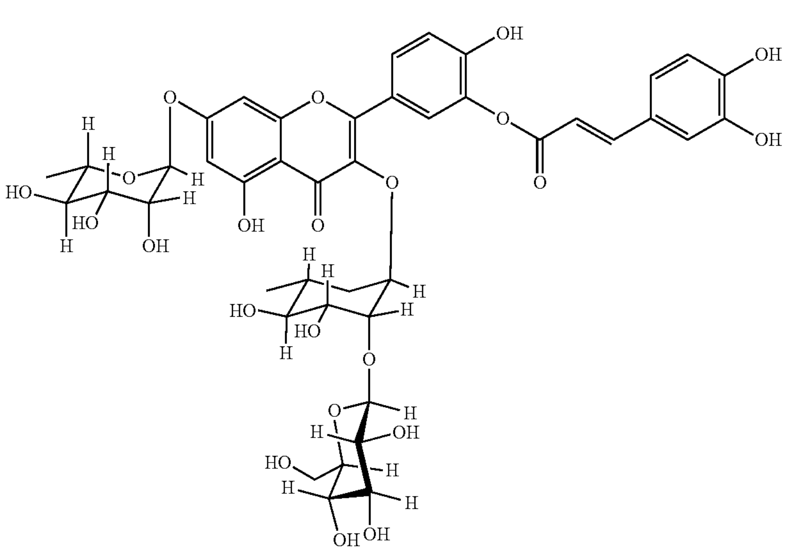

As shown in EXAMPLE 4, caffeic acid in compound 2 was esterified at C-4' of flavonol. Considering the reaction specificity of the esterification enzyme, there should be present at least a trace amount of the compound represented by FORMULA (3), which composes $R_1$=rhamnose residue, $R_2$=glucose residue-rhamnose residue, and $R_3$=OH in GENERAL FORMULA (A), and was confirmed to be a new compound.

[F27]

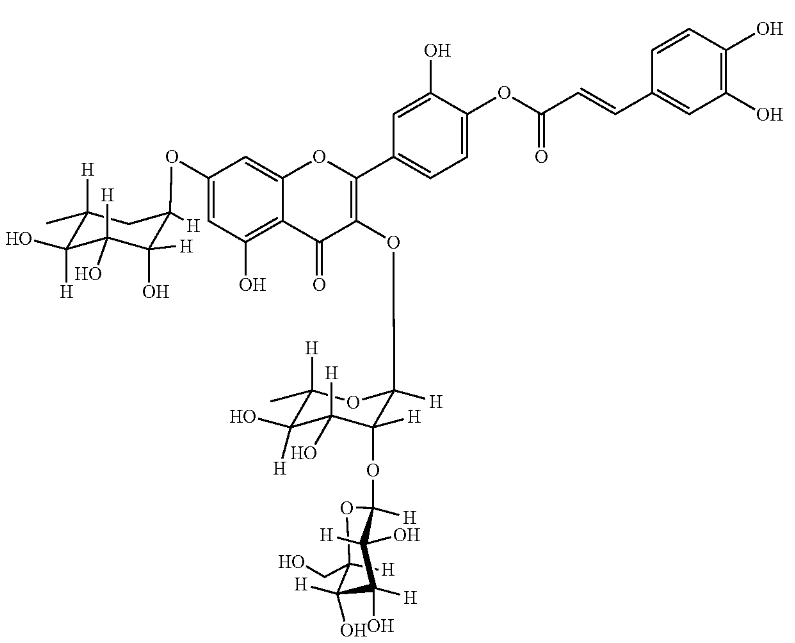

(3)

Example 6

(Structural Determination of Compound 4)

Compound 4 (purified), obtained in EXAMPLE 2, was dissolved in MeOH (0.1 mg/mL) and analyzed by HRESI-MS (+). As a result, the $(M+Na)^+$ ion peak was observed at m/z 811.16941, and the molecular formula of compound 4 was determined as $C_{36}H_{36}O_{20}$ ($C_{36}H_{36}O_{20}Na$, calcd. for 811.16976 (D 4.31 ppm)).

Figure 8:
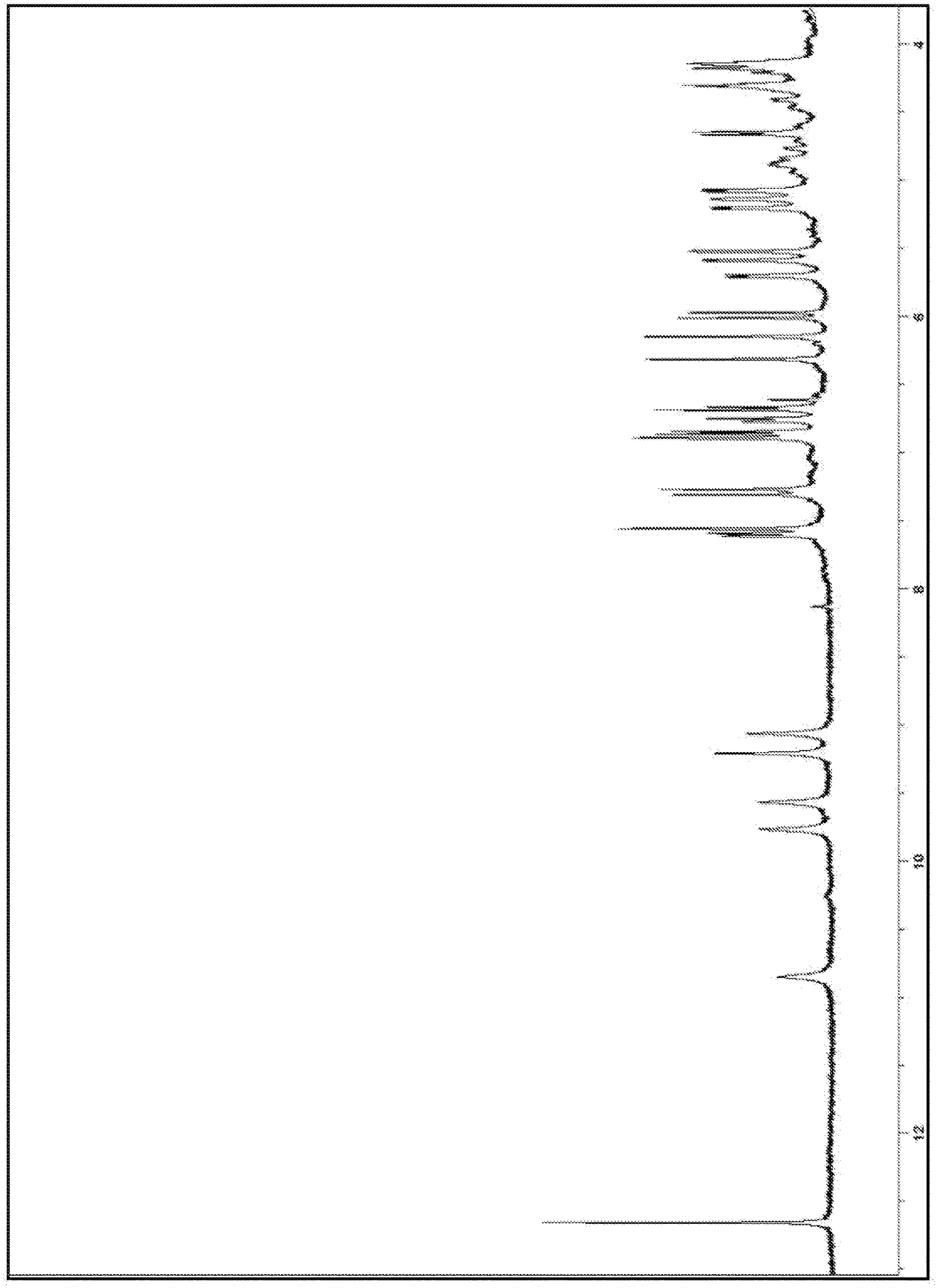
FIG. 8 $^1$H-NMR spectrum (in DMSO-$d_6$) of compound 4.
Figure 9:
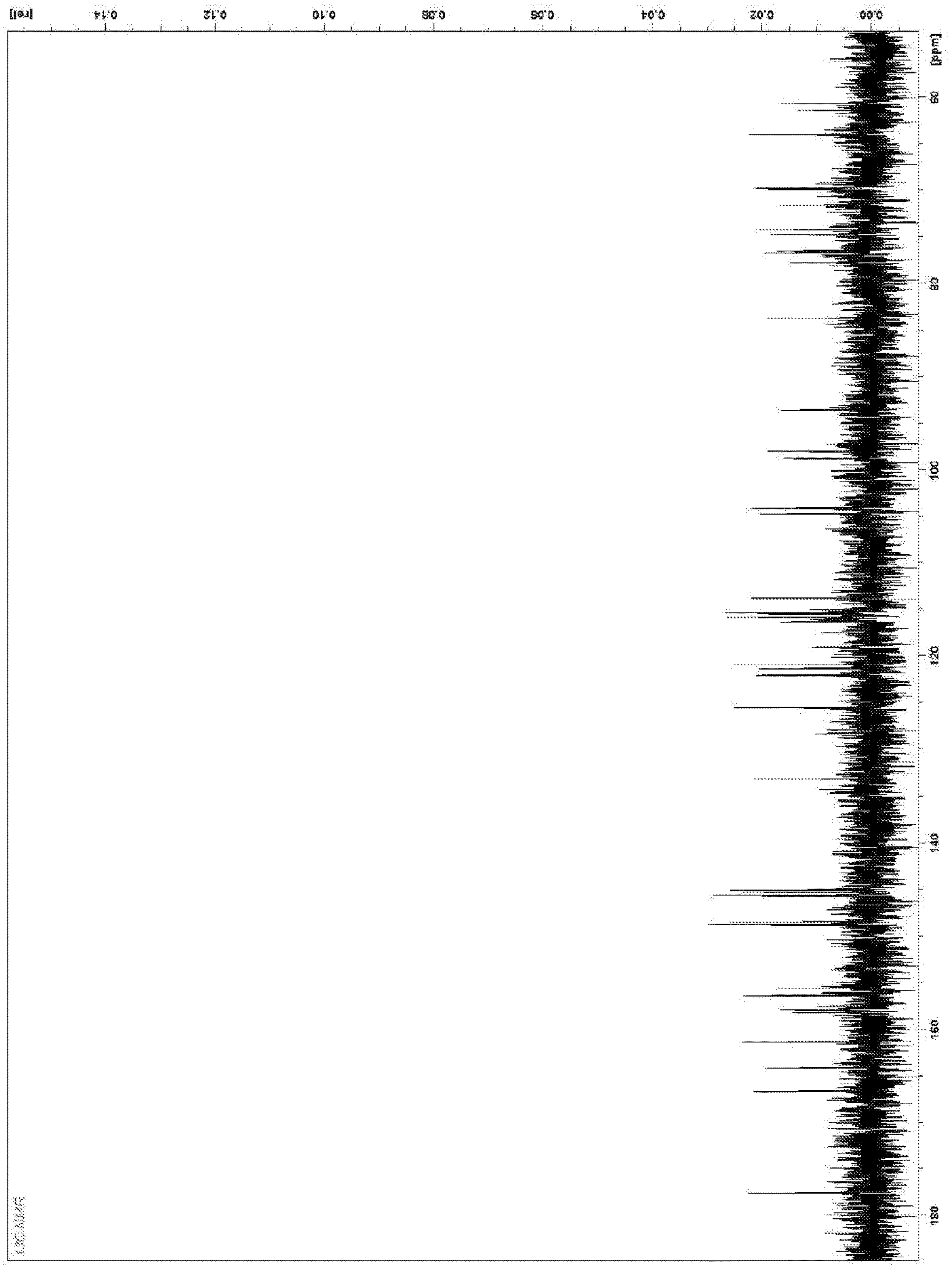
FIG. 9 $^{13}$C-NMR spectrum (in DMSO-$d_6$) of compound 4.

Compound 4 (10 mg) was dissolved in DMSO-$d_6$ (1 mL), and analyzed by 1D ($^1H$ NMR (FIG. 8) and $^{13}C$ NMR (FIG. 9)) and 2D ($^1H$-$^1H$ DQF COSY, HMQC, HMBC, NOESY, TOCSY, and J-resolved HSQC).

Through analyses of these spectra, the structure of compound 4 was determined as that shown in FORMULA (8). Compound 4 composes $R_1$=H and $R_2$=glucose residue-glucose residue in GENERAL FORMULA (B), and was confirmed to be a novel compound.

[F28]

(8)

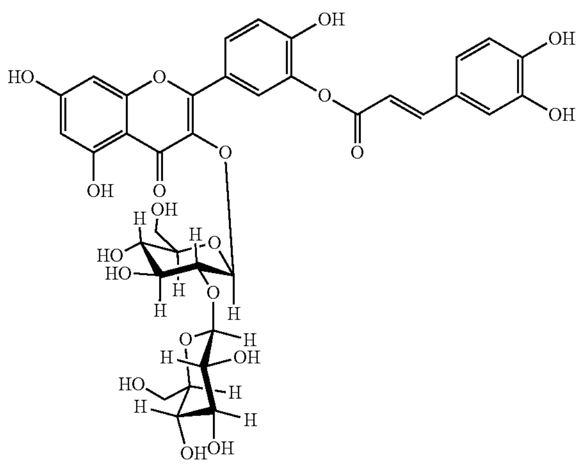

As shown in EXAMPLE 4, caffeic acid in compound 2 was esterified at C-4' of flavonol. Considering the reaction specificity of the esterification enzyme, there should be present at least a trace amount of the compound represented by FORMULA (4), which composes $R_1$=H, $R_2$=glucose residue-glucose residue, and $R_3$=OH in GENERAL FORMULA (A), and was confirmed to be a new compound.

[F29]

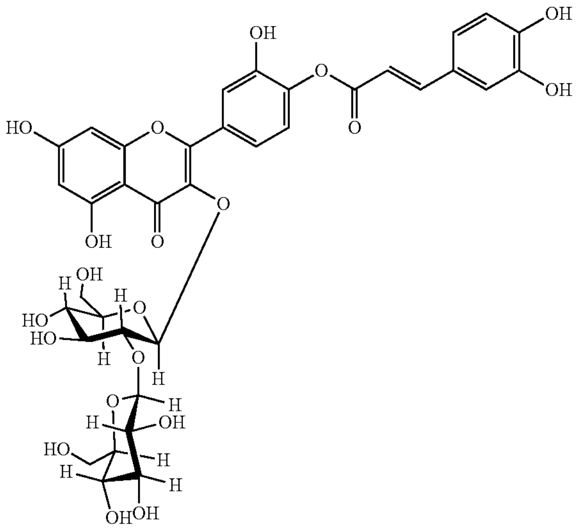

Example 7

(Structural Determination of Compound 5)

Compound 5 (purified), obtained in EXAMPLE 2, was dissolved in MeOH (0.1 mg/mL) and analyzed by HRESI-MS (+). As a result, the $(M+Na)^+$ ion peak was observed at m/z 957.2266, and the molecular formula of compound 5 was determined as $C_{42}H_{46}O_{24}$ ($C_{42}H_{46}O_{24}Na$, calcd. for 957.2268 (D 2.08 ppm)).

Figure 10:
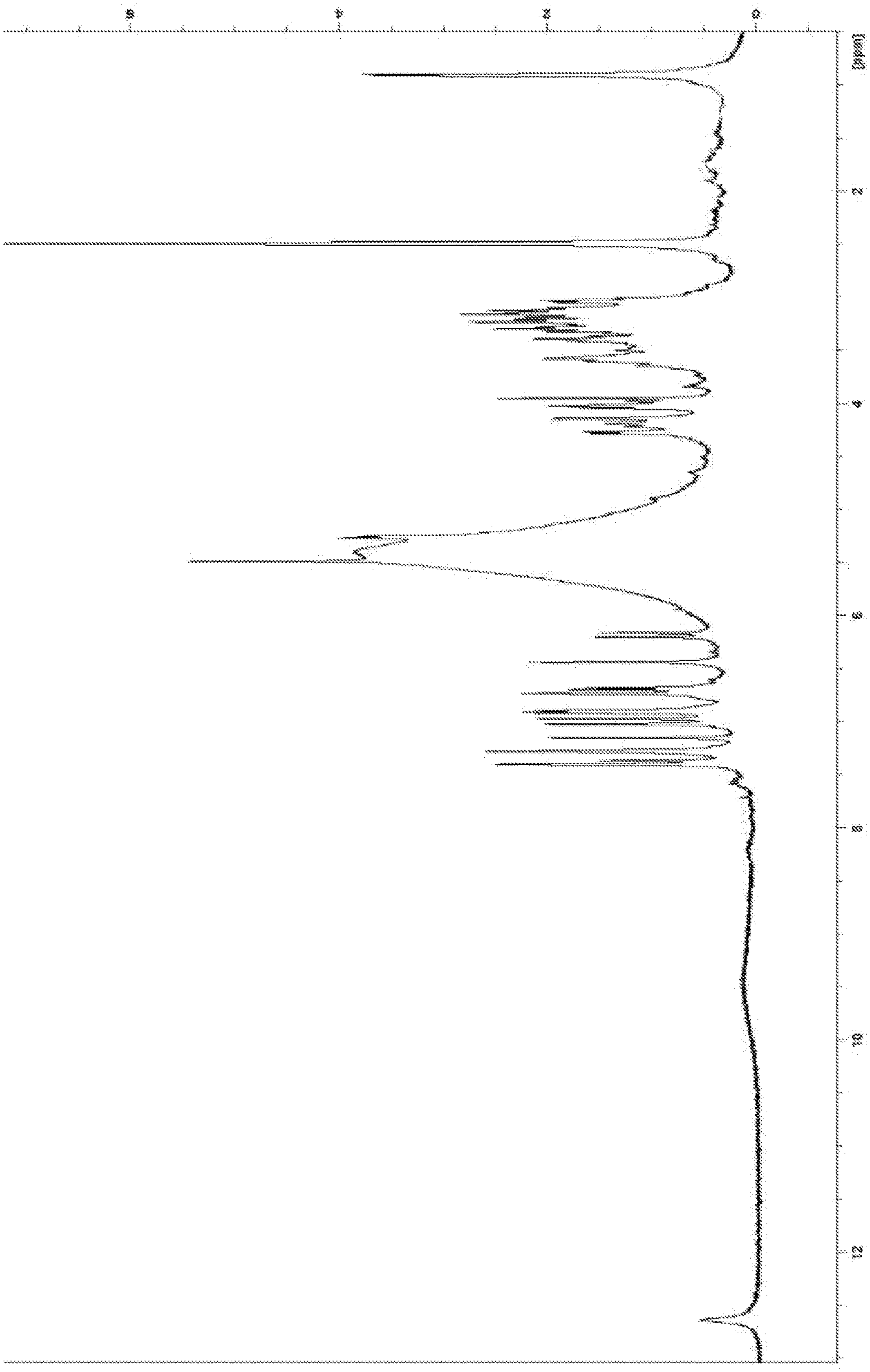
FIG. 10 $^1$H-NMR spectrum (in DMSO-$d_6$) of compound 5.
Figure 11:
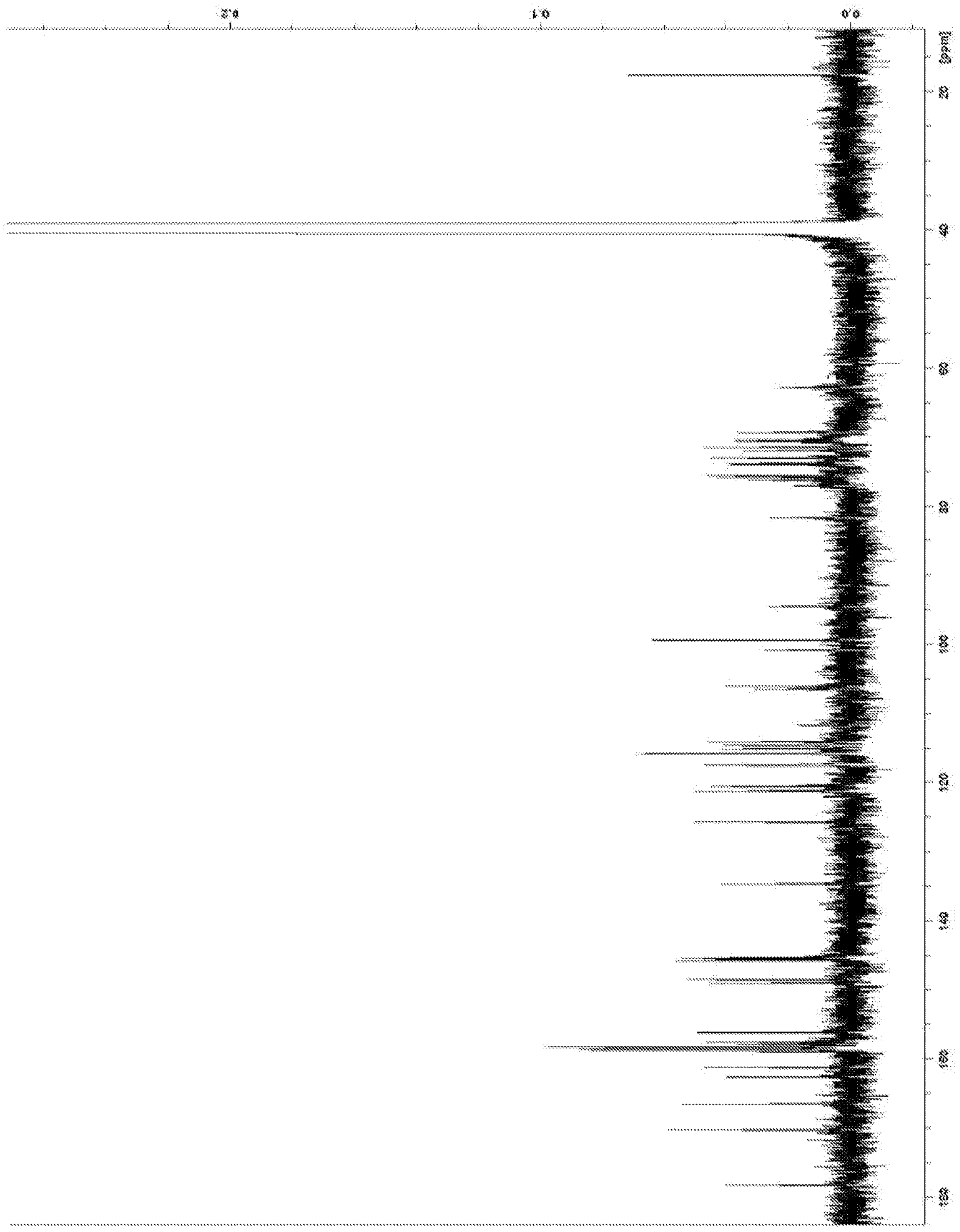
FIG. 11 $^{13}$C-NMR spectrum (in DMSO-$d_6$) of compound 5.

Compound 5 (10 mg) was dissolved in DMSO-$d_6$ (1 mL), and analyzed by 1D ($^1$NMR (FIG. 10) and $^{13}$C NMR (FIG. 11)) and 2D ($^1$H-$^1$H DQF COSY, HMQC, HMBC, NOESY, TOCSY, and J-resolved HSQC). Through analyses of these spectra, the structure of compound 5 was determined as that shown in FORMULA (9).

Compound 5 composes $R_1$=glucose residue and $R_2$=glucose residue-rhamnose residue in GENERAL FORMULA (B), and was confirmed to be a novel compound.

[F30]

(9)

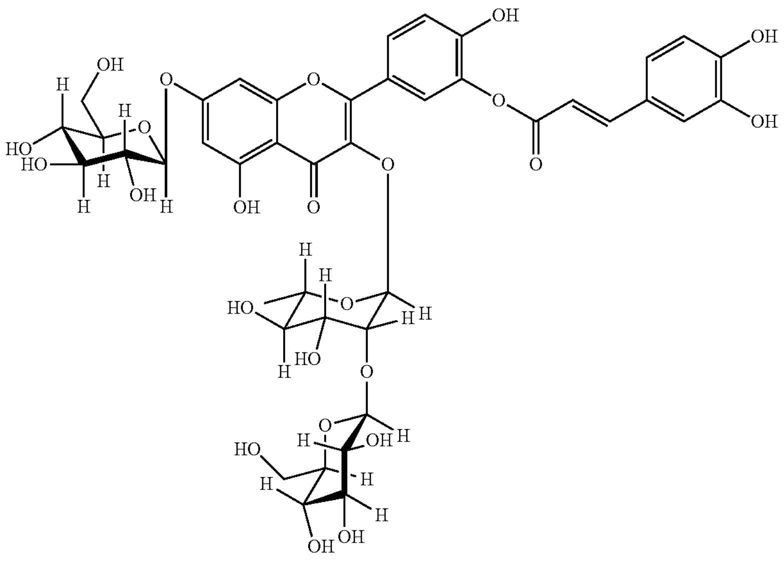

As shown in EXAMPLE 4, caffeic acid in compound 2 was esterified at C-4' of flavonol. Considering the reaction specificity of the esterification enzyme, there should be present at least a trace amount of the compound represented by FORMULA (5), which composes $R_1$=glucose residue, $R_2$=glucose residue-rhamnose residue, and $R_3$=OH in GENERAL FORMULA (A), and was confirmed to be a new compound.

[F31]

(5)

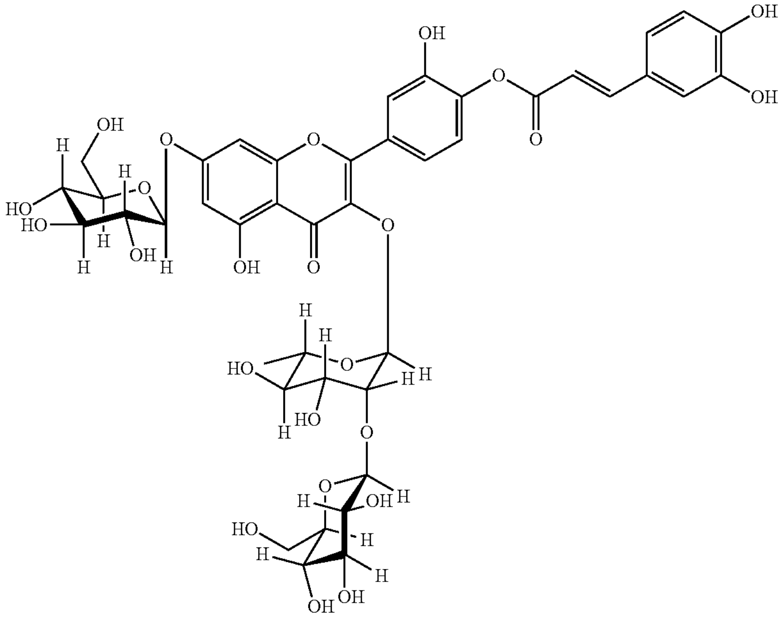

Example 8

(Other Aromatic Compound Glycosides)

Results shown in EXAMPLE 1 (refer to FIG. 1) and in EXAMPLEs 2-7 show that aromatic compound glycosides, i.e., the compounds represented by FORMULAs (1)-(9), are included in the *freesia* 'Ishikawa f2 go'. In GENERAL FORMULAs (A) and (B), we exemplify aromatic compound glycosides as follows: ($R_3$ is included only in (A).)

Compound 1 (GENERAL FORMULA (B): FORMULA (6)) $R_1$: rhamnose residue, $R_2$: glucose residue-glucose residue Compound 2 (GENERAL FORMULA (A): FORMULA (2)) $R_1$: rhamnose residue, $R_2$: glucose residue-glucose residue, $R_3$: H Compound 3 (GENERAL FORMULA (B): FORMULA (7)) $R_1$: rhamnose residue, $R_2$: glucose residue-rhamnose residue Compound 4 (GENERAL FORMULA (B): FORMULA (8)) $R_1$: H, $R_2$: glucose residue-glucose residue Compound 5 (GENERAL FORMULA (B): FORMULA (9)) $R_1$: glucose residue, $R_2$: glucose residue-rhamnose residue Compound 6 (GENERAL FORMULA (A): FORMULA (1)) $R_1$: rhamnose residue, $R_2$: glucose residue-glucose residue, $R_3$: OH Compound 7 (GENERAL FORMULA (A): FORMULA (3)) $R_1$: rhamnose residue, $R_2$: glucose residue-rhamnose residue, $R_3$: OH Compound 8 (GENERAL FORMULA (A): FORMULA (4)) $R_1$: H, $R_2$: glucose residue-glucose residue, $R_3$: OH Compound 9 (GENERAL FORMULA (A): FORMULA (5)) $R_1$: glucose residues $R_2$: glucose residue-rhamnose residues $R_3$: OH Results shown in EXAMPLE 1 (refer to FIG. 1) and in EXAMPLEs 2-7 also show that further aromatic compound glycosides should be included in the *freesia* 'Ishikawa f2 go', besides the compounds represented by FORMULAs (1)-(9). In GENERAL FORMULAs (A) and (B), we exemplify aromatic compound glycosides as follows:

Compound 10 (GENERAL FORMULA (B)) $R_1$: rhamnose residues $R_2$: rhamnose residue-glucose residue Compound 11 (GENERAL FORMULA (A)) $R_1$: rhamnose residues $R_2$: rhamnose residue-glucose residues $R_3$: OH Compound 12 (GENERAL FORMULA (A)) $R_1$: glucose residues $R_2$: glucose residue-glucose residues $R_3$: H Compound 13 (GENERAL FORMULA (A)) $R_1$: rhamnose residues $R_2$: glucose residue-rhamnose residues $R_3$: H Compound 14 (GENERAL FORMULA (B)) $R_1$: glucose residues $R_2$: rhamnose residue-glucose residue Compound 15 (GENERAL FORMULA (A)) $R_1$: glucose residues $R_2$: rhamnose residue-glucose residues $R_3$: OH Compound 16 (GENERAL FORMULA (B)) $R_1$: H, $R_2$: glucose residue-rhamnose residue Compound 17 (GENERAL FORMULA (A)) $R_1$: H, $R_2$: glucose residue-rhamnose residues $R_3$: OH Compound 18 (GENERAL FORMULA (A)) $R_1$: H, glucose residue-rhamnose residues $R_3$: H Compound 19 (GENERAL FORMULA (A)) $R_1$: glucose residues $R_2$: glucose residue-glucose residue, $R_3$: OH Example 9

(Confirmation of Antioxidative Function of Compounds 1-5)

The lipid peroxidation-inhibiting assay with rat brain homogenate is an experimental system for evaluating damages of biological system caused by the generation of ROS (Reactive Oxygen Species). It is because the rat brain is an organ that is easily oxidized by ROS. Using this system, we evaluated antioxidative activity of compounds 1-5.

Using rat brain homogenate, we examined lipid peroxidation-inhibiting activities of the test compounds. It was performed by incubating rat brain homogenate to proceed with lipid peroxidation reactions, with each compound and with no compound (as the control), by measuring the amounts of consequently generated malondialdehyde by absorbance at 532 nm in the TBA method, and by comparing the amounts of the malondialdehyde products between them.

(Peroxidation-Inhibiting Test of Rat Brain Lipids)

We preincubated IWAKI disposable test tube (03 mm×100 mm) that contained 0.6 mL of 100 mM phosphate buffer (pH 7.4), 0.05 mL of each test sample-including solution, 0.1 mL of 1 mM ascorbic acid, and 0.05 mL of distilled water at 37° C. for 5 min. And 0.2 mL of 2.5% (w/v) rat brain homogenate was added to the test tube, and incubated for 1 hour at 37° C. with shaking (150 rpm). Then, 1 mL of 0.2 N HCl solution including 20% (W/V) trichloroacetic acid and 0.5% (W/V) 2-thiobarbituric acid was added to the above test tube to stop the reaction. Next, this test tube containing each reaction solution was boiled for 30 min at 100° C. to produce color. After chilled on ice, each solution from the test tube was centrifuged with 3,000 rpm for 10 min, and the absorbance of each supernatant was measured at 532 nm ($A_{532}$).

The lipid peroxidation-inhibiting ratio (%) of each extracted solution (containing each flavonoid glycoside as a test compound (T)) was calculated using the following Formula 1.

$$(1-[T-B]/[C-B])'100. \quad \text{Formula 1}$$

T (test), C (control), and B (blank) are $A_{532}$ of a test compound with the rat brain homogenate, the control (no compound (instead ethanol) with the homogenate), and the blank control (no compound (instead ethanol) without the homogenate (instead phosphate buffer)), respectively. The lipid peroxidation-inhibiting activity was determined as the $IC_{50}$ value, representing the concentration at which 50% inhibition was observed.

We showed the $IC_{50}$ values (mM; 50% inhibition concentration of rat brain lipid-peroxidation) of compounds 1-5 in Table 1. Compounds 1-5 were all revealed to retain the lipid peroxidation-inhibiting activity. According to this, the aromatic compound glycosides of the present invention, especially compounds 1-5, were confirmed to possess potent antioxidant activities.

TABLE 1

| Compound | $IC_{50}$ (μM) |
|---|---|
| compound 1 | 1.7 |
| compound 2 | 15 |
| compound 3 | 1.4 |
| compound 4 | 1.1 |
| compound 5 | 1.5 |

Example 10

(Extraction of Aromatic Compound Glycosides from *Freesia* 'Kayak')

'Kayak', a horticulture variety with yellow petals, was ordinarily cultivated in green houses of Ishikawa Agriculture and Forestry Research Center. Large amounts (146.72 g) of the 'Kayak' flowers (whole flowers containing petals, sepals, stamens, and pistils) were harvested in the early part of April.

The raw *freesia* flowers were extracted by adding $CH_2Cl_2$ (dichloromethane)-MeOH (methanol) (1:1) (1 L) and by stirring for 30 min at room temperature in dim light, and then filtrated under reduced pressure. MeOH (1 L) was added to the filtrated debris, and treated same. Further, 50% (V/V) MeOH (1 L) was added to the filtrated debris, and treated same.

Thirty μL of each extract (before concentration) was analyzed by HPLC, whose condition is as follows.

Column: Develosil $C_{30}$-UG, 5 μm (NOMURA CHEMICAL) 20 mm×250 mm

Solvent: 17% (V/V) $CH_3CN$ (acetonitrile)+0.1% (V/V) TFA (trifluoroacetic acid)

Flow rate: 8.0 mL/min

Detection: DAD (diode array detector) 200-600 nm.

Figure 13:
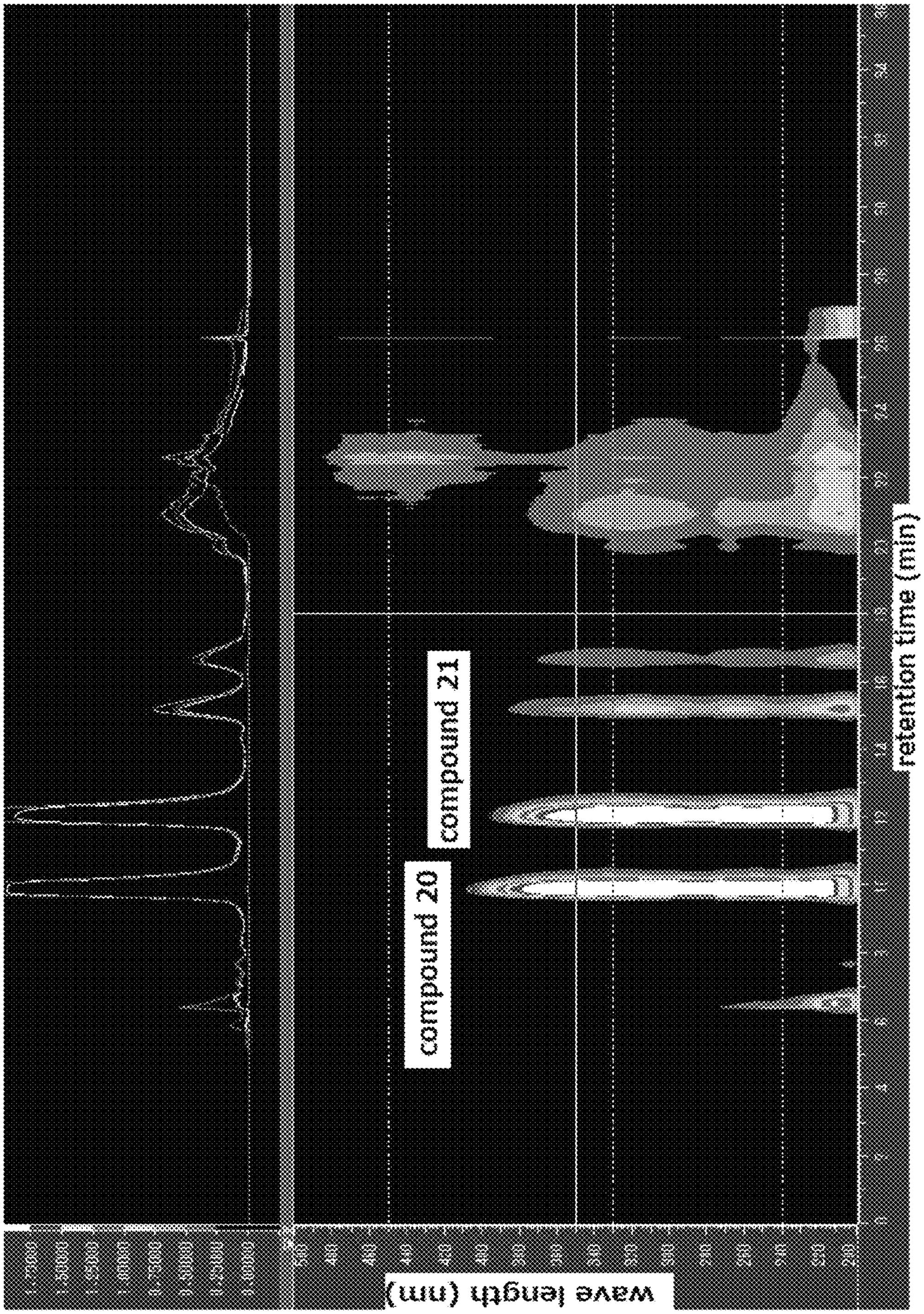
FIG. 13 HPLC analytical results of a *freesia* (Kayak) flower extract.

As the results of this HPLC analysis, we confirmed that two flavonoid (aromatic compound (polyphenol)) glycosides, designated compound 20 and compound 21, exist as the major products only in 50% MeOH extract, as shown in FIG. 13.

As for other *freesia* cultivars 'Passat' and 'Boulevard', the 50% MeOH extracts of their flowers were analyzed by HPLC with the same condition. Consequently, the two flavonoid glycosides same to those of 'Kayak' (compounds 20 and 21) were confirmed to exist.

Example 11

(Isolation and Purification of Aromatic Compound Glycosides Included in *Freesia* 'Kayak')

The 50% MeOH extract of 'Kayak' that was prepared in EXAMPLE 10 was concentrated to dryness (2.63 g). 15 mL of 17% (V/V) $CH_3CN$ was added to this sample, treated with an ultrasonicator, and the supernatant was obtained after centrifugation at 7,000 rpm for 10 min. Two major flavonoid glycosides dissolved in the supernatant were isolated as the individual 50 μL eluates by preparative HPLC using the conditions described in EXAMPLE 10, and concentrated to dryness.

Consequently, compound 20 (213.6 mg, RT (retention time) 9.7 min) and compound 21 (294.8 mg, RT 12.2 min) were obtained as the pure compounds.

In addition to these two compounds, several flavonoid glycosides further existed in the 50% MeOH extract (FIG. 13). Other yellow-flower varieties 'Passart' and 'Boulevard' retained the same compounds.

Example 12

(Structural Determination of Compound 20)

Compound 20 (purified), obtained in EXAMPLE 11, was dissolved in MeOH (0.1 mg/mL) and analyzed by HRESI-MS (−). As a result, the $(M-H)^-$ ion peak was observed at m/z 963.20260, and the molecular formula of compound 20 was determined as $C_{42}H_{44026}$ ($C_{42}H_{43}O_{26}$, calcd. for 963.204265 (D 1.73 ppm)).

Figure 14:
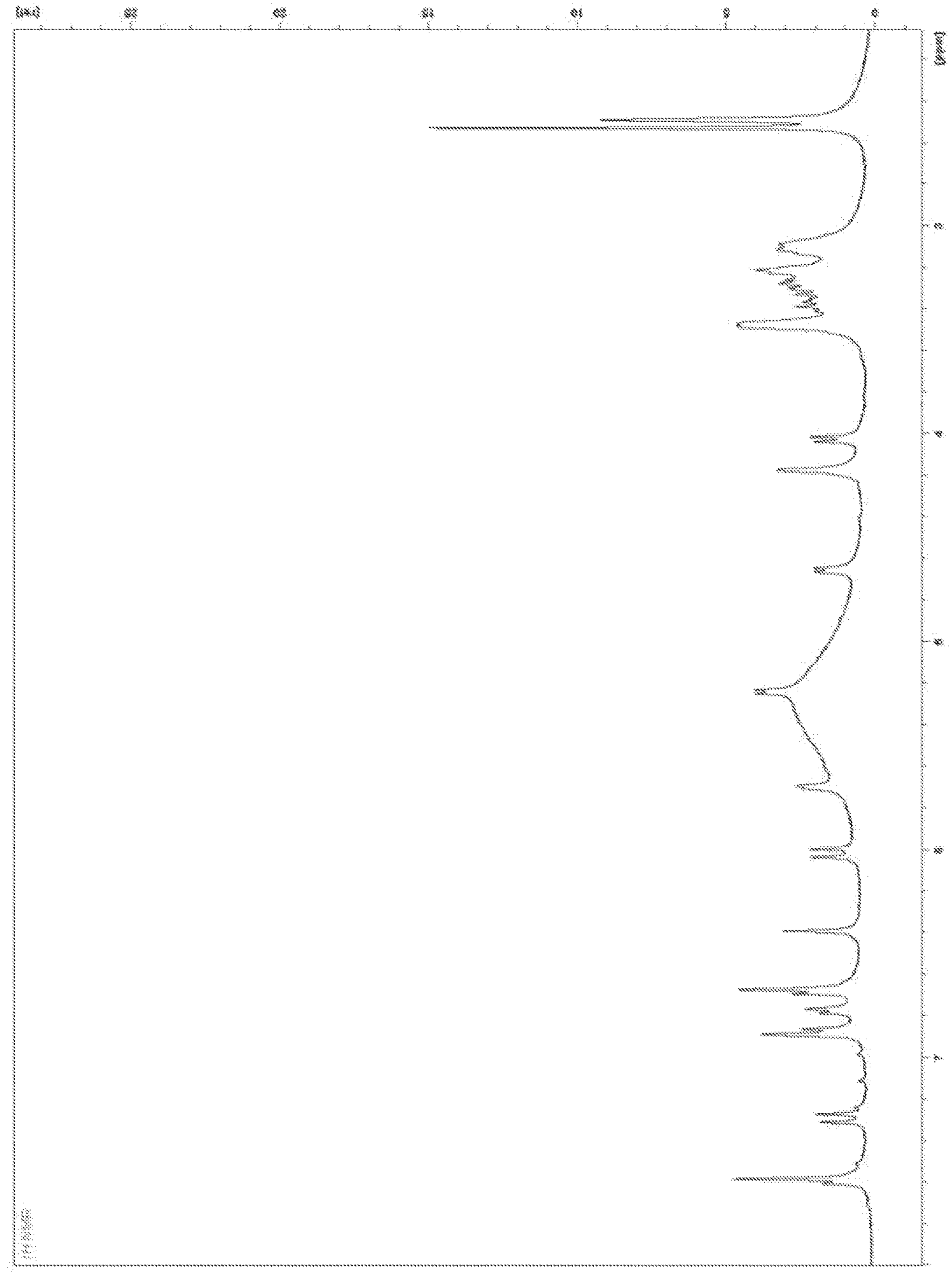
FIG. 14 $^1$H-NMR spectrum of compound 20.
Figure 15:
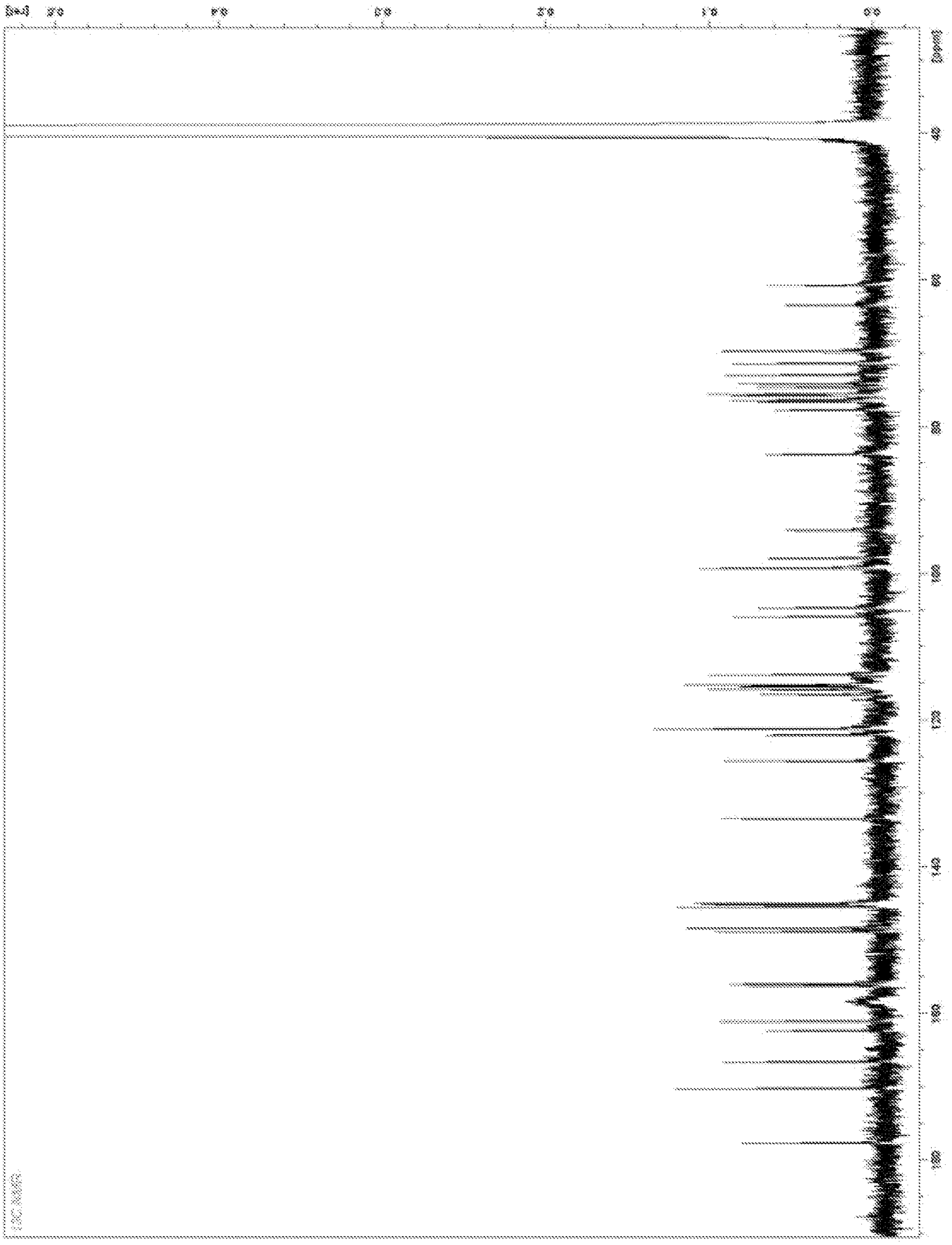
FIG. 15 $^{13}$C-NMR spectrum of compound 20.

Compound 20 (10 mg) was dissolved in DMSO-$d_6$ (1 mL), and analyzed by 1D ($^1$H NMR (FIG. 14) and $^{13}$C NMR (FIG. 15)) and 2D ($^1$H-$^1$H DQF COSY, HMQC, HMBC, NOESY, TOCSY, and J-resolved HSQC). Through analyses of these spectra, the structure of compound 20 was determined as that shown in FORMULA (10).

Compound 20 composes $R_1$=glucuronic acid residue and $R_2$=glucose residue-glucose residue—in GENERAL FORMULA (B), and was confirmed to be a novel compound.

Example 13

(Structural Determination of Compound 21)

Compound 21 (purified), obtained in EXAMPLE 11, was dissolved in MeOH (0.1 mg/mL) and analyzed by HRESI-MS (−). As a result, the $(M-H)^-$ ion peak was observed at m/z 947.20790, and the molecular formula of compound 21 was determined as $C_{42}H_{44}O_{25}$ ($C_{42}H_{43}O_{25}$, calcd. for 947.20935 (D 1.53 ppm)).

Figure 16:
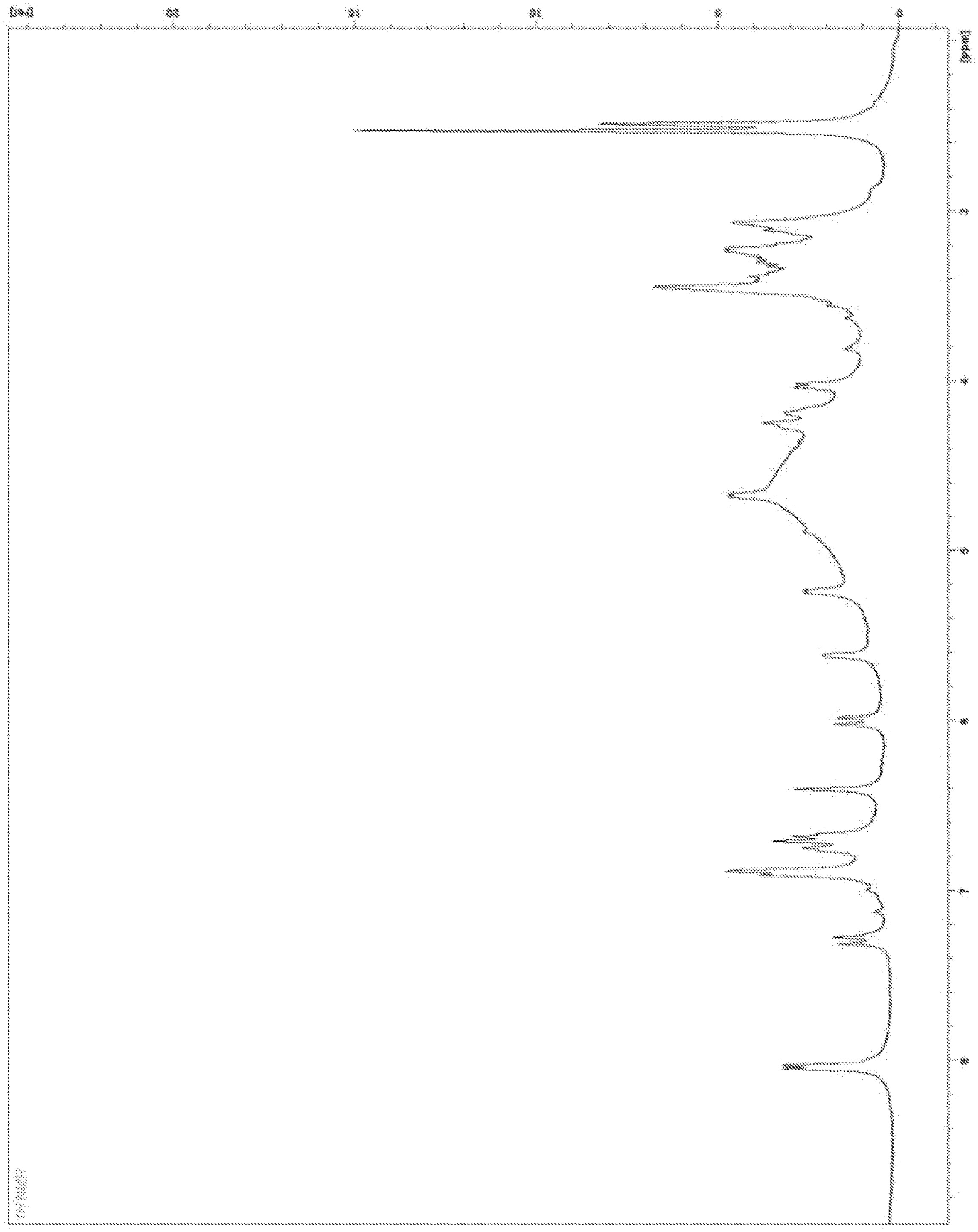
FIG. 16 $^1$H-NMR spectrum of compound 21.
Figure 17:
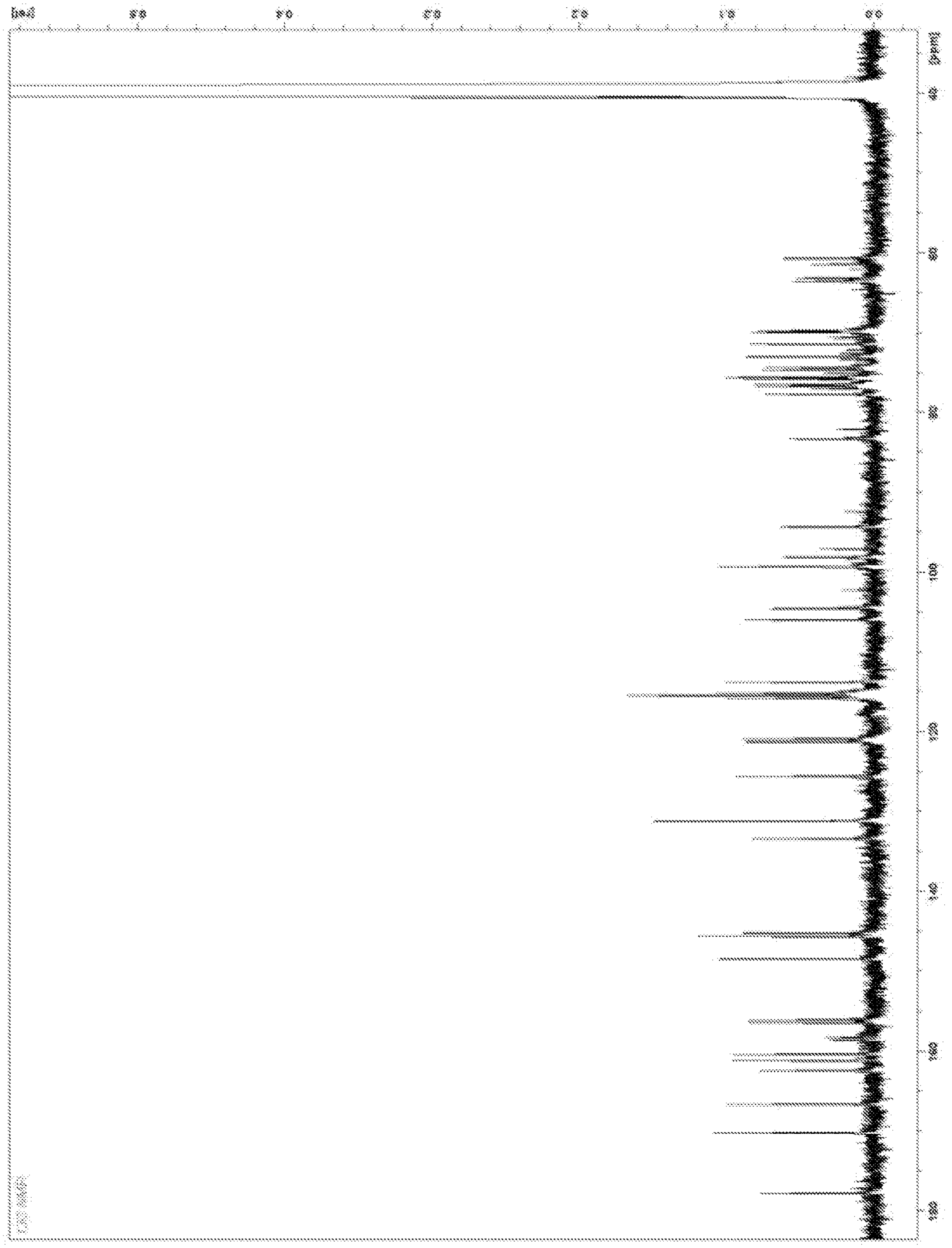
FIG. 17 $^{13}$C-NMR spectrum of compound 21.

Compound 21 (10 mg) was dissolved in DMSO-$d_6$ (1 mL), and analyzed by 1D ($^1$H NMR (FIG. 16) and $^{13}$C NMR (FIG. 17)) and 2D ($^1$H-$^1$H DQF COSY, HMQC, HMBC, NOESY, TOCSY, and J-resolved HSQC). Through analyses of these spectra, the structure of compound 21 was determined as that shown in FORMULA (11).

Compound 21 composes $R_1$=glucuronic acid residue, $R_2$=glucose residue-glucose residue, and $R_3$=H in GENERAL FORMULA (A), and was confirmed to be a novel compound.

Example 14

(Other Aromatic Compound Glycosides)

Compound 20 and compound 21 are clarified to include glucuronic acid in the molecule. In GENERAL FORMULAS (A) and (B), we exemplify such aromatic compound glycosides as follows:

Compound 20 (GENERAL FORMULA (B): FORMULA (10)) $R_1$: glucuronic acid residue, $R_2$: glucose residue-glucose residue Compound 21 (GENERAL FORMULA (A): FORMULA (11)) $R_1$: glucuronic acid residue, $R_2$: glucose residue-glucose residue, $R_3$: H Compound 22 (GENERAL FORMULA (B)) $R_1$: glucuronic acid residue, $R_2$: glucose residue-rhamnose residue Compound 23 (GENERAL FORMULA (A)) $R_1$: glucuronic acid residue, $R_2$: glucose residue-rhamnose residue, $R_3$: H Compound 24 (GENERAL FORMULA (B)) $R_1$: glucuronic acid residue, $R_2$: rhamnose residue-glucose residue Compound 25 (GENERAL FORMULA (A)) $R_1$: glucuronic acid residue, $R_2$: rhamnose residue-glucose residue, $R_3$: H Compound 26 (GENERAL FORMULA (A)) $R_1$: glucuronic acid residue, $R_2$: glucose residue-glucose residue, $R_3$: OH Compound 27 (GENERAL FORMULA (A)) $R_1$: glucuronic acid residue, $R_2$: glucose residue-rhamnose residue, $R_3$: OH Compound 28 (GENERAL FORMULA (A)) $R_1$: glucuronic acid residue, $R_2$: rhamnose residue-glucose residue, $R_3$: OH Example 15

(Peroxidation-Inhibiting Test of Rat Brain Lipids)

As for antioxidative activity of compounds 20 and 21, we examined the peroxidation-inhibiting activity of rat brain lipids. This result is shown in Table 2. These two compounds were found to possess peroxidation-inhibiting activity. This activity was higher with compound 20 than with compound 21.

TABLE 2

| Compound | $IC_{50}$ (μM) |
|---|---|
| compound 20 | 1.5 |
| compound 21 | 23 |

Example 16

(Differentiation-Inducing Test of Mouse Preadipocyte 3T3-L1)

Mouse preadipocyte 3T3-L1 is used for screening of activities for lipid metabolism improvement and anti-diabetes, since 3T3-L1 is induced to the differentiation of small adipocyte under proper conditions. This differentiated fat cell produces lipid bodies that can be stained with Oil Red O. PPAR (Peroxisome Proliferator-Activated Receptor) belongs to nuclear receptor superfamily. PPARγ is importantly related to differentiation of fat cells, e.g., activated PPARγ promotes differentiation from preadipocyte to adipocyte. Furthermore, PPARγ promotes apoptosis of large fat cells. Compounds activating PPARγ (PPARγ agonists) improve insulin resistance by inducing apoptosis of large fat cells that are willing to produce TNF-α and free fatty acids, reluctant to import sugars, and induce insulin resistance. PPARγ agonists further reduce blood glucose levels, and exert anti-diabetes activity by inducing differentiation to small fat cells that are reluctant to produce TNF-α and free fatty acids, willing to import glucose in blood, and improve glucose metabolism. Currently, PPARγ agonists such as rosiglitazone (thiazolidine) are used clinically to treat patients with type-2 diabetes mellitus.

Compounds that possess strong activity for differentiation to small fat cells possess effects for improving lipid metabolism and for preventing and improving type-2 diabetes mellitus.

In the present EXAMPLE, we carried out to examine whether aromatic compound glycosides can promote differentiation to small fat cells, using mouse 3T3-L1 preadipocyte.

Thus, we examined the PPARγ agonistic activities of compounds 3, 4, 20, and 21, which were selected as the representatives.

The 3T3-L1 cell line was purchased from Japanese Collection of Research Bioresources Cell Bank (JCRB, Osaka, Japan). The 3T3-L1 cells were cultured in DMEM with 10% fetal calf serum (FCS, Sigma Aldrich, St Lous, USA) and antibiotics (62.5 mg/ml penicillin and 100 mg/ml streptomycin). The cells were seeded in collagen coated 12-well plates at 10,000 cells/well (1 mL) and grown to confluence for 2 days. The differentiation procedure was initiated 2 days after cells reached confluence by changing the medium to the differentiation cocktail (10 mg/ml insulin in DMEM containing 10% FBS and antibiotics) with or without various concentrations of test compounds (positive control, thiazolidine; four aromatic compound glycosite) dissolved in DMSO ($10^3$-$10^4$ times dilutions of the stocks were used). Thereafter, the cells were grown in the differentiation cocktail for 6 days.

Figure 18:
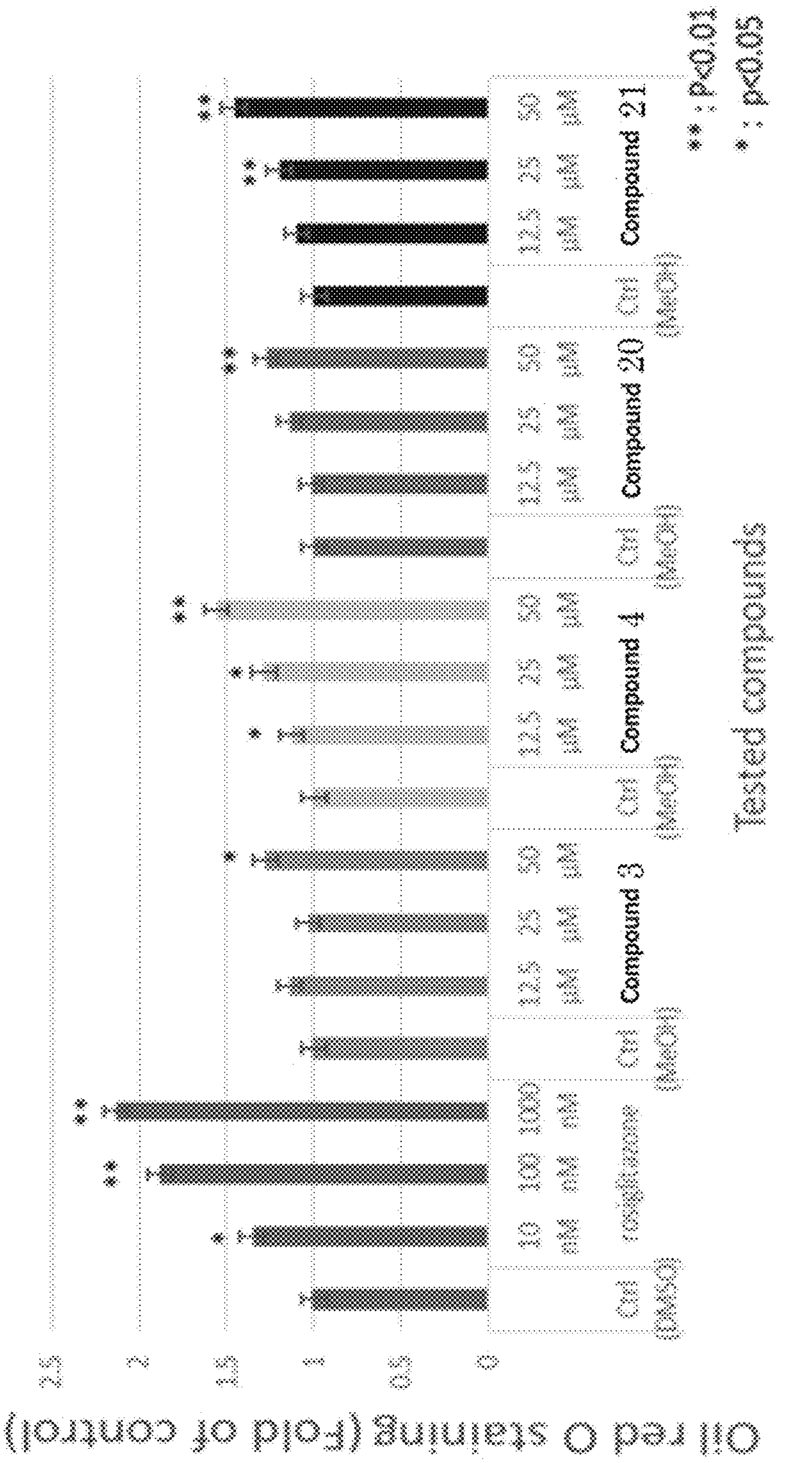
FIG. 18 Test results of differentiation induction of aromatic compound glycosides by use of 3T3-L1 cells.

Then, Oil Red O (ORO) staining was performed to evaluate the ratio of the differentiated 3T3-L1 cells. Individual wells, from which culture medium was removed, were fixed with 1 mL of 10% (v/v) formalin for 1 hour and washed four times with 1 mL of water. The cells were then rinsed with 1 mL of 60% isopropanol for 5 min followed by the incubation with freshly prepared ORO working solution (0.5 g of ORO in 100 ml of isopropanol was added 67 ml of water, and filtered through 0.45 mm filter) for 15 min. After four times washing with PBS (1 ml). ORO was then extracted from fixed cells with 100% isopropanol (1 mL), and $OD_{500}$ values of isopropanol solution, which reflect the ORO amount imported into the cells (=the lipid (body) amount of the differentiated cells), were measured by 96-well microplate reader. Relative lipid content of each well was represented as percentage with the correspondent control as 100% (FIG. 18).

Consequently, the tested four aromatic compound glycosides, i.e., compounds 3, 4, 20, and 21 were all clarified to retain strong activity for differentiation induction to small fat cells (adipose), i.e., compounds 3, 4, 20, and 21 possess effects for improving lipid metabolism and for preventing and improving type-2 diabetes mellitus.

INDUSTRIAL APPLICABILITY

The invention provides a novel aromatic compound glycoside, and an antioxidant composition, a lipid metabolism-improving composition, or a diabetes-prophylactic/ameliorating composition, each containing the glycoside.

The invention claimed is:

1. An extracted flavonoid compound represented by formula (B):

[F1]

(B)

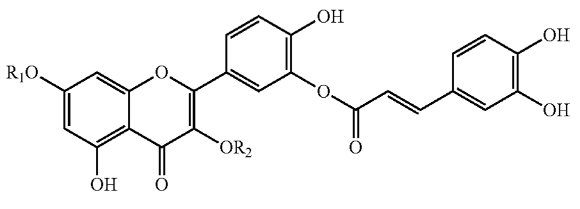

wherein R1 represents a rhamnose residue, a glucose residue, a glucuronic acid residue, or H; R2 represents a rhamnose residue, a glucose residue, H, a glucose residue-glucose residue, a glucose residue-rhamnose residue, or a rhamnose residue-glucose residue.

2. An extracted flavonoid compound selected from at least one of the following compounds represented by formula (2):

[F3]
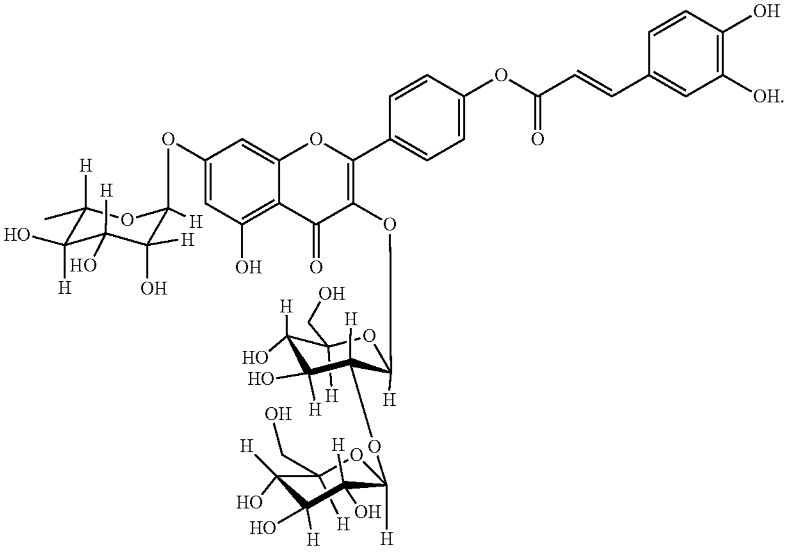
(2)
or a compound represented by formula (1):
[F8]
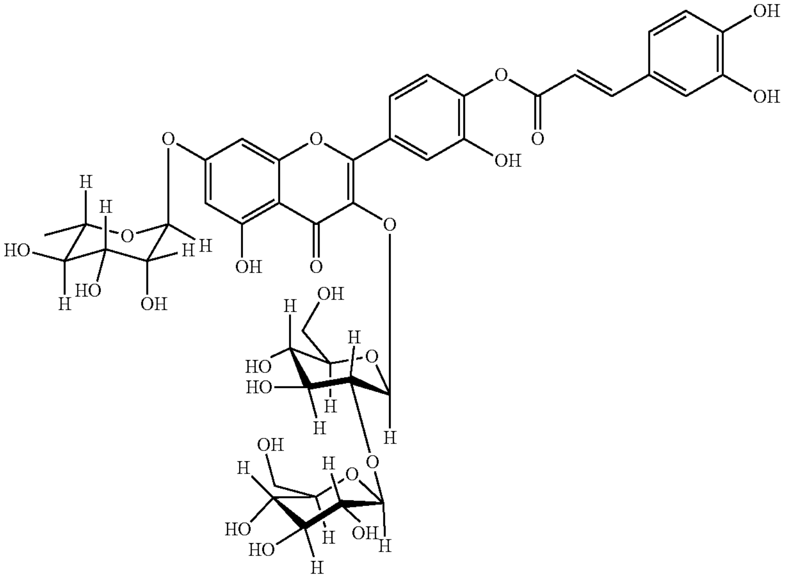
(1)

or a compound represented by formula (3):
[F9]
(3)
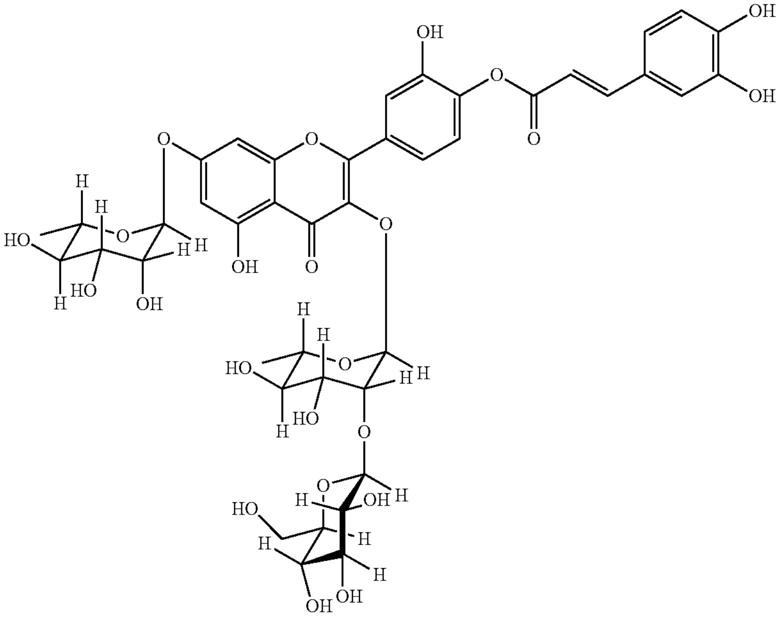
or a compound represented by formula (4):
[F10]
(4)
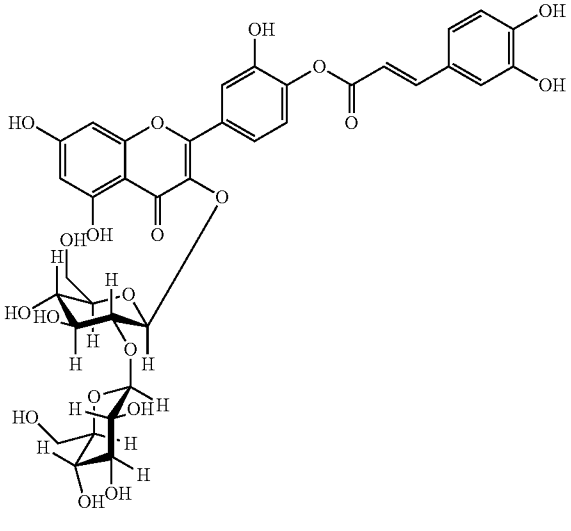

or a compound represented by formula (5):
[F11]
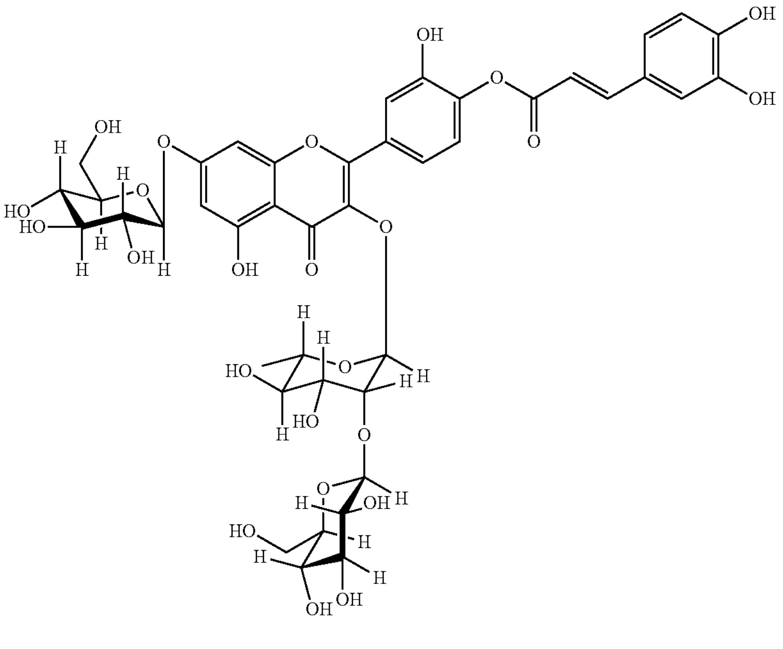
(5)
or a compound represented by formula (11):
[F13]
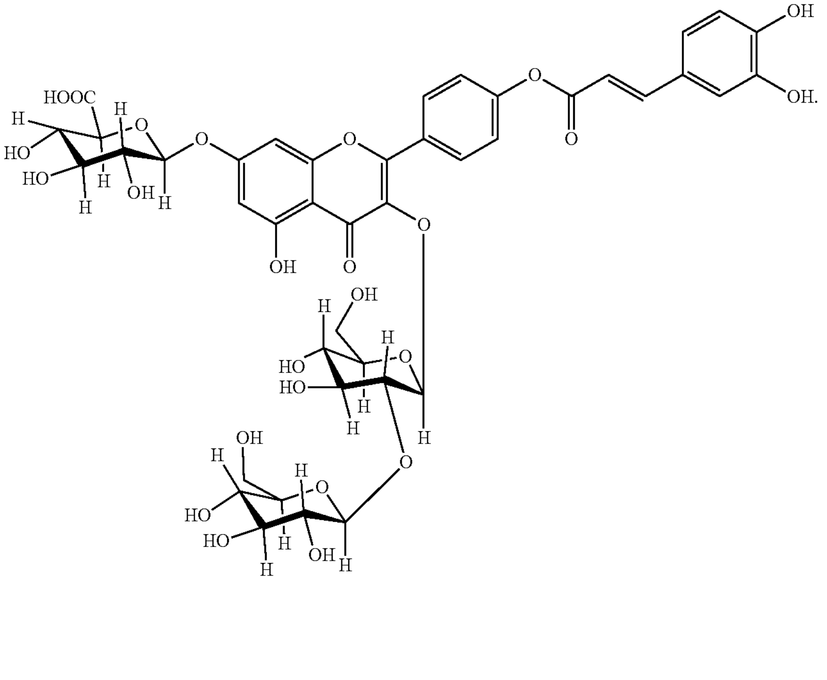
(11)

3. The extracted flavonoid compound according to claim 2, which is the compound represented by the formula (2):
[F3]
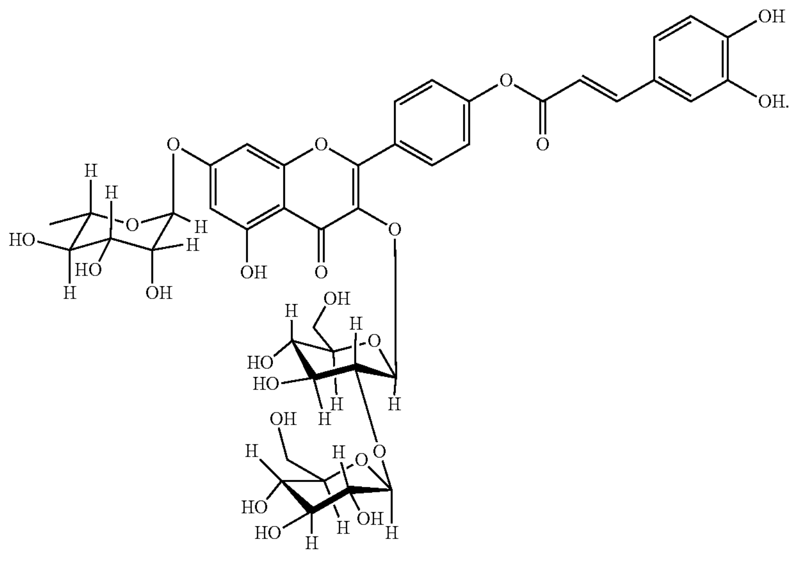
(2)
4. The extracted flavonoid compound according to claim 1, which is a compound represented by formula (6):
[F4]
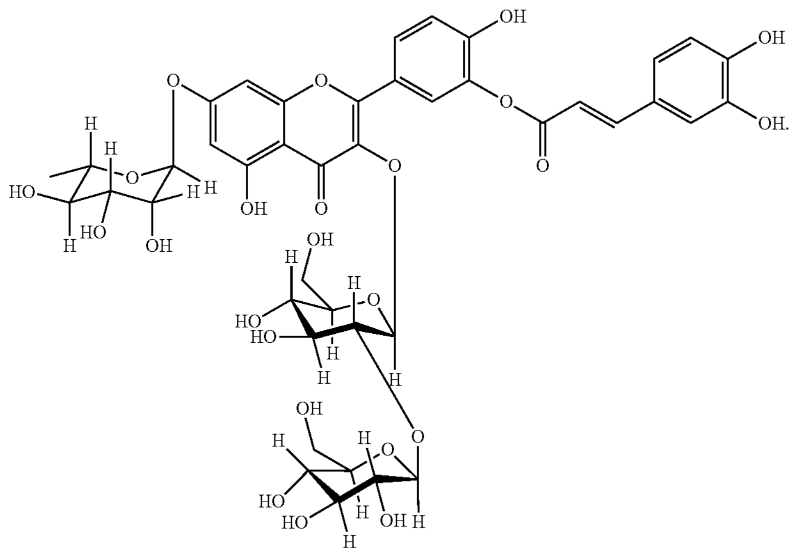
(6)

5. The extracted flavonoid compound according to claim 1, which is a compound represented by formula (7):
[F5]
(7)
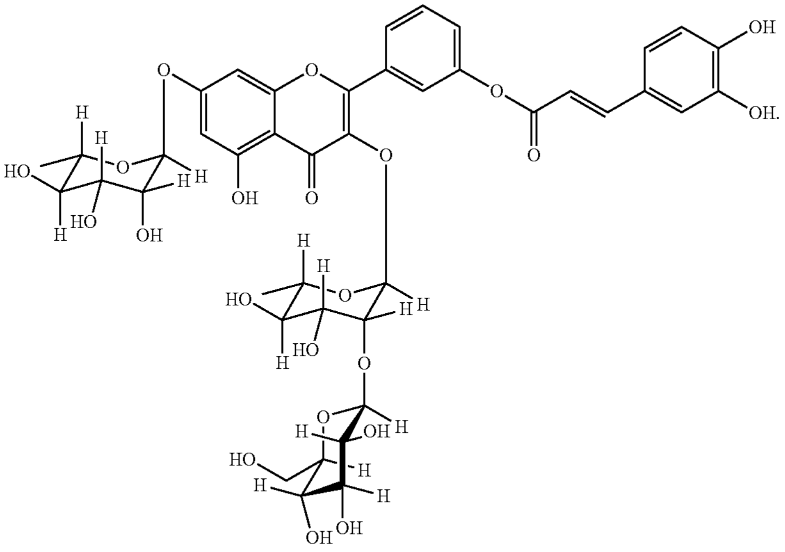
6. The extracted flavonoid compound according to claim 1, which is a compound represented by formula (8):
[F6]
(8)
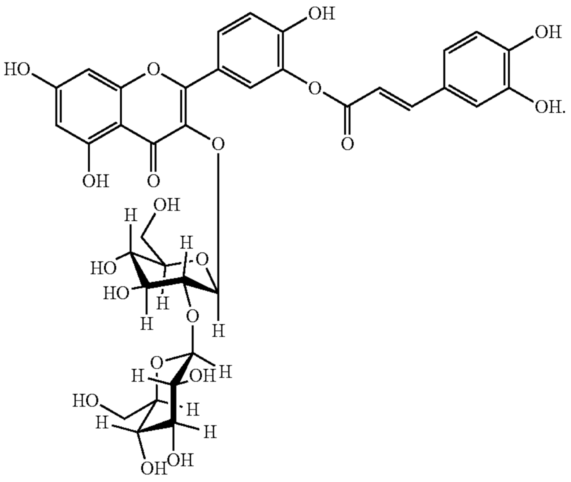

7. The extracted flavonoid compound according to claim 1, which is a compound represented by formula (9):
[F7]
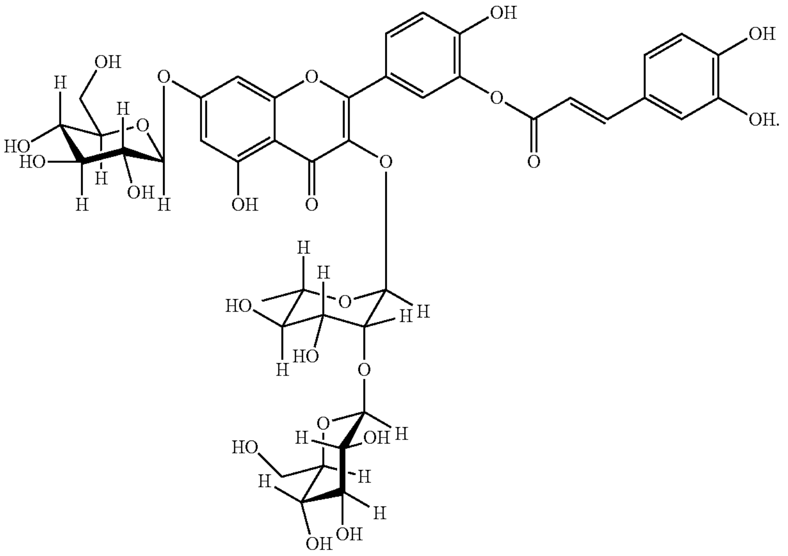
(9)
8. The extracted flavonoid compound according to claim 2, which is the compound represented by the formula (1):
[F8]
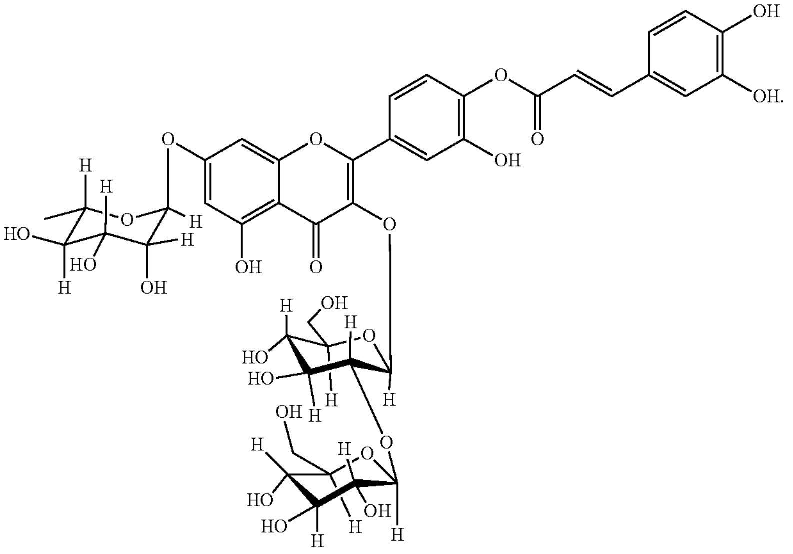
(1)

9. The extracted flavonoid compound according to claim 2, which is the compound represented by the formula (3):
[F9]
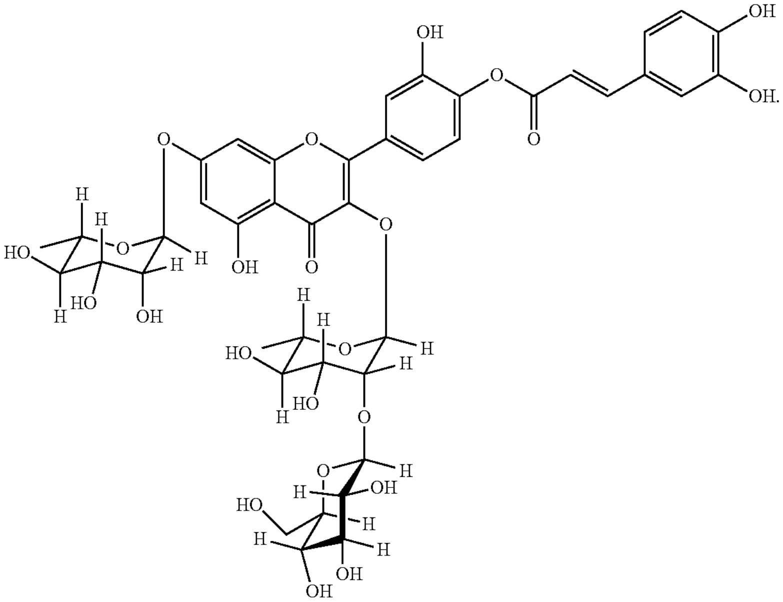
(3)
10. The extracted flavonoid compound according to claim 2, which is the compound represented by the formula (4):
[F10]
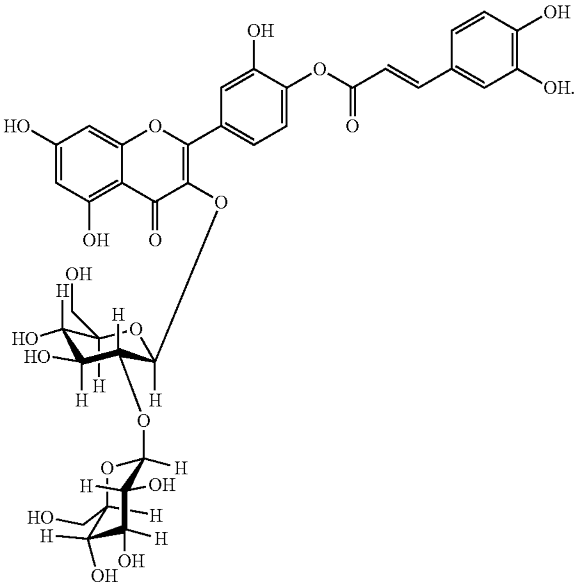

11. The extracted flavonoid compound according to claim 2, which is the compound represented by the formula (5):
[F11]
(5)
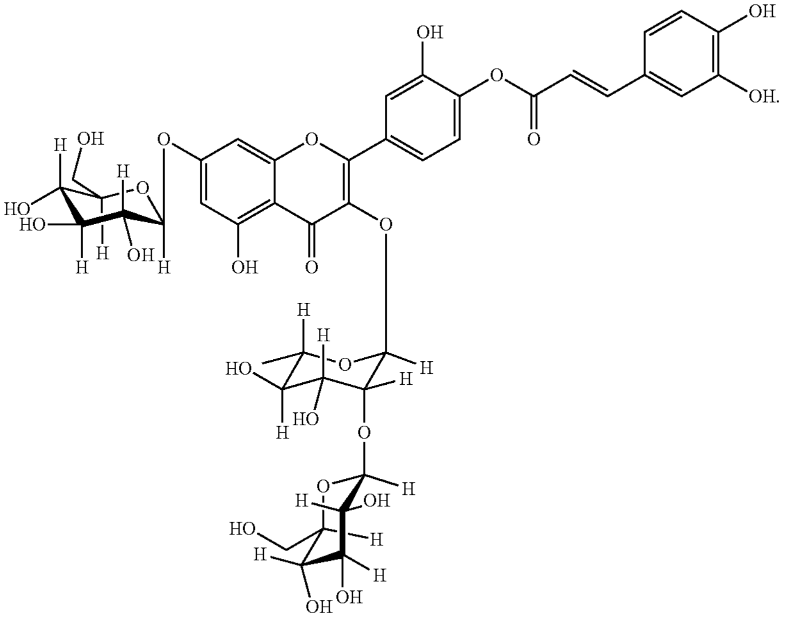
12. The extracted flavonoid compound according to claim 1, which is a compound represented by formula (10):
[F12]
(10)
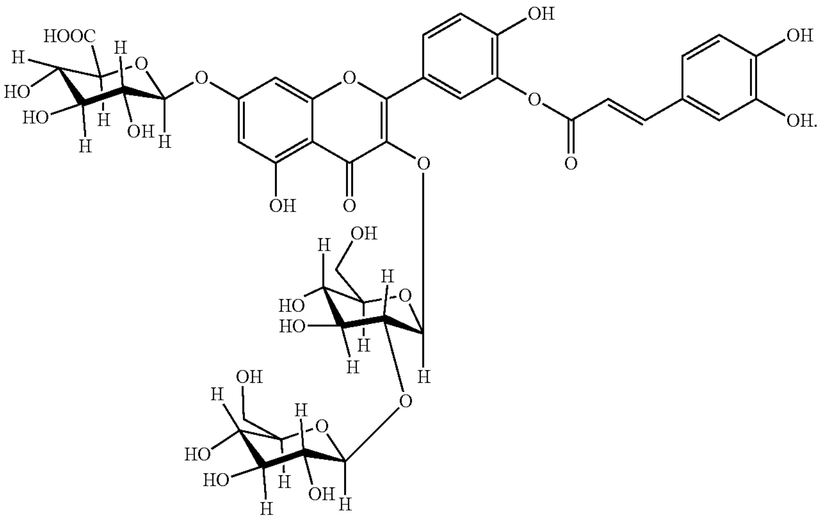

13. The extracted flavonoid compound according to claim 2, which is the compound represented by the formula (11):

[F13]

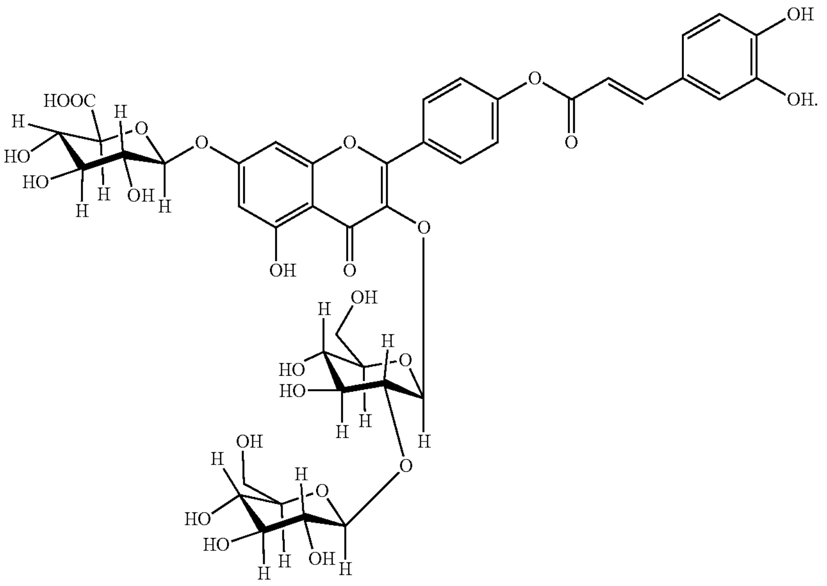
(11)

14. An antioxidant composition which contains the extracted flavonoid compound as recited in claim 1.

15. A lipid metabolism-improving composition, which contains the extracted flavonoid compound as recited in claim 1.

16. A diabetes-prophylactic/ameliorating composition, which contains the extracted flavonoid compound as recited in claim 1.

17. A method for producing an aromatic compound glycoside, the method comprising a step of extracting the extracted flavonoid compound as recited in claim 1.

18. The method according to claim 17, wherein the plant which can produce an aromatic compound is *freesia.*

19. The method according to claim 18, wherein the *freesia* is yellow *freesia.*

20. The method according to claim 19, wherein the yellow *freesia* is a cultivar of airy flora-airy yellow (Ishikawa f2), Aladin, Porto passat, Gold flame, Kayak, Spring time, or Boulevard.

* * * * *